US006750171B2

(12) United States Patent
Hoge, II et al.

(10) Patent No.: US 6,750,171 B2
(45) Date of Patent: Jun. 15, 2004

(54) SYNTHESIS OF P-CHIRAL BISPHOSPHOLANE LIGANDS AND THEIR TRANSITION METAL COMPLEXES FOR USE AS ASYMMETRIC HYDROGENATION CATALYSTS

(75) Inventors: Garrett Stewart Hoge, II, Ann Arbor, MI (US); Om Prakash Goel, Ann Arbor, MI (US)

(73) Assignee: Warner-Lambert Company LLC, Morris Plains, NJ (US)

( * ) Notice: Subject to any disclaimer, the term of this patent is extended or adjusted under 35 U.S.C. 154(b) by 0 days.

(21) Appl. No.: 10/418,684

(22) Filed: Apr. 18, 2003

(65) Prior Publication Data

US 2003/0236433 A1 Dec. 25, 2003

Related U.S. Application Data

(62) Division of application No. 10/021,610, filed on Dec. 12, 2001, now Pat. No. 6,605,745.
(60) Provisional application No. 60/255,329, filed on Dec. 13, 2000.

(51) Int. Cl.$^7$ .............................. B01J 31/24; C07F 9/50
(52) U.S. Cl. .......................... 502/162; 502/165; 556/13
(58) Field of Search ............................ 556/13; 568/12; 502/150, 162, 165, 166

(56) References Cited

U.S. PATENT DOCUMENTS

| | | | | | |
|---|---|---|---|---|---|
| 5,008,457 A | * | 4/1991 | Burk | ............................ | 568/12 |
| 5,250,731 A | * | 10/1993 | Burk | ............................ | 564/150 |
| 6,337,406 B1 | * | 1/2002 | Zhang | ........................ | 549/220 |
| 6,492,544 B2 | * | 12/2002 | Krimmer et al. | ............ | 560/170 |

FOREIGN PATENT DOCUMENTS

| | | |
|---|---|---|
| WO | WO 99/24444 | 5/1999 |
| WO | WO 99/62917 | 12/1999 |
| WO | WO 00/11008 | 3/2000 |

OTHER PUBLICATIONS

J Amer. Chem. Soc by Mark Burk vol. 115 pp. 10125–10138 1993.*
Organometallics by Mark Burk vol. 19 pp. 250–260 2000.*
CA: 136354979 by Holz et al abs of European Journal of Org. Chem. (24) pp. 4615–4624 2001.*
CA: 130:338253 abs of WO 9924444 May 1999.*
Burk, Mark J., "The DuPHOS Ligands—A Hisotrical Account", Chemtracts, Oct. 1998, pp. 787–802.
Vineyard, B.D., et al, "Asymmetric Hydrogenation, Rhodium Chiral Bisphosphine Catalyst", Journal of the American Chemical Society, 1977, 99:18: pp. 5946–5952.
Brunner, Henri, "Enantioselective Synthesis with Optically Active Transition–Metal Catalysts", Synthesis, 1988, pp. 645–654.

Burk, Mark J., "C2–Symmetric Bis(phospholanes) and Their Use in Highly Enantioselective Hydrogenation Reactions", American Chemical Society, 1991, 113; pp. 8518–8519.
Nugent, William A.. et al, "Beyond Nature's Chiral Pool: Enantioselective Catalysis in Industry", Science, vol. 259, 1993; pp. 479–483.
Burk, Mark J., et al, "Preparation and Use of C2–Symmetric Bis(phospholanes): Production of a–Amino Acid Derivatives via Highly Enantioselective Hydrogenation Reaction", American Chemical Society, 1993; 115; pp. 10125–10138.
Knowles, W.S., et al, Journal of the American Chemical Society, 1975;97: 2567–2568.
Burk, Mark J., "Highly Enantioselective Hydrogenation of B–Keto Esters under Mild Conditions", American Chemical Society, 1995: 117; pp. 4423–4424.
Ohashi, Atusushi, et al, "1–tert–Butyl–2–methylphospholane–borane and its coupling product 2,2'bis(1–tert–butylphospholane–borane)", Acta Cryst., 2000, C56, pp. 723–725.
Burk, Mark J., et al, "Bis(phospholane) Ligands Containing Chiral Backbones. Matching and Mismatching Effects in Enantioselective Hydrogenation of a–Keto Esters", Organometallics, 2000; 19; pp. 250–260.
Burk, Mark J., et al, "Practical Access to 2–Alkylsuccinates through Asymmetric Catalytic Hydrogenation of Stobbe–Derived Itaconates**", Angew, Chem. Int. Ed., 1998, 37, No. 13/14; pp. 1931–1933.
Burk, Mark J., et al, "A Three–Step Procedure for Assymetric Catalytic Reductive Amidation of Ketones", J. Org. Chem., 1998, 63; pp. 6084–6085.
Imamoto, Tsuneo, et al, "P–Chiral Bis(trialkylphosphine) Ligands and Their Use in Highly Enantioselective Hydrogenation Reactions", J. Am. Chem. Soc., 1998, 120; pp. 1635–1636.
Zhu, Guoxin, et al, "Highly Enantioselective Rh–Catalyzed Hydrogenations with a New Chiral 1,4–Bisphosphine Containing a Cyclic Backbone", J. Am. Chem. Soc., 1997, 119; pp. 1799–1800.
Burk, Mark J., et al, "Rh–DuPHOS–Catalyzed Enantioselective Hydrogenation of Enol Esters. Application to the Synthesis of Highly Enantioenriched a–Hydroxy Esters and 1,2–Diols", J. Am. Chem. Soc., 1998, 120; pp. 4345–4353.
Yuen, Po–wai, et al, "Enantioselective Synthesis of PD114723: A Potent Seterospecific Anticonvulsant.", Bioorganic & Medicinal Chemistry Letters, 1994,vol. 4, No. 6; pp. 823–826.

(List continued on next page.)

Primary Examiner—Jean F Vollano
(74) Attorney, Agent, or Firm—Matthew J. Russo; Karen DeBenedictia

(57) ABSTRACT

P-chiral bisphospholane ligands and methods for their preparation are described. Use of metal/P-chiral bisphospholane complexes to catalyze asymmetric transformation reactions to provide high enantiomeric excesses of formed compounds is also described.

11 Claims, No Drawings

OTHER PUBLICATIONS

Burk, Mark J., et al., "New Chiral Phospholanes; Synthesis, Characterization, and Use in Asymetric Hydrogenation Reactions", Tetrahedron Asymmetry, vol. 2, No. 7, 1991; pp. 569–592.

PCT International Search Report for PCT/IB01/02419.

Polniaszek, R. P., "Preparation of (2S*,5S*)–2,5–Dibenzylphospholanic Acid", J. Org. Chem., 1992, vol. 57; pp. 5189–5195; ISSN: 0022–3263; XP002195096.

Borleske, Stephen G., et al, "Carboxy Derivatives of Five–Membered Cyclic Phosphorus Compounds 1" Phosphorus, 1975, vol. 5, pp. 173–182; ISSN 0308–664X; XP008001659.

* cited by examiner

SYNTHESIS OF P-CHIRAL BISPHOSPHOLANE LIGANDS AND THEIR TRANSITION METAL COMPLEXES FOR USE AS ASYMMETRIC HYDROGENATION CATALYSTS

This application is a division of commonly assigned U.S. application Ser. No. 10/021,610, filed Dec. 12, 2001, now U.S. Pat. No. 6,605,745, which claims the benefit of U.S. Provisional Application No. 60/255,329, filed Dec. 13, 2000, now abandoned the complete disclosures of which are herein incorporated by reference for all purposes.

FIELD OF THE INVENTION

This invention relates to P-chiral bisphospholane ligands and methods for their preparation. In addition, this invention relates to the formation of metal/P-chiral bisphospholane complexes that catalyze asymmetric transformation reactions to generate high enantiomeric excesses of formed compounds.

BACKGROUND OF THE INVENTION

There is a growing trend in the pharmaceutical industry to market chiral drugs in enantiomerically pure form in order to provide desired positive effects in humans. Production of enantiomerically pure compounds is important for several reasons. First, one enantiomer often provides a desired biological function through interactions with natural binding sites, but another enantiomer typically does not have the same function or effect. Further, it is possible that one enantiomer has harmful side effects, while another enantiomer provides a desired positive biological activity. To meet this demand for chiral drugs, many approaches for obtaining enantiomerically pure compounds have been explored such as diastereomeric resolution, structural modification of naturally occurring chiral compounds, asymmetric catalysis using synthetic chiral catalysts and enzymes, and the separation of enantiomers using simulated moving bed (SMB) technology.

Asymmetric catalysis is often the most efficient method because a small amount of a chiral catalyst can be used to produce a large quantity of a chiral target molecule. Over the last two decades, more than a half-dozen commercial industrial processes have been developed that use asymmetric catalysis as the key step in the production of enantiomerically pure compounds with a tremendous effort focused on developing new asymmetric catalysts for these reactions (Morrison J. D., ed. *Asymmetric Synthesis*, Academic Press: New York, 1985:(5); Bosnich B., ed. *Asymmetric Catalysis*, Martinus Nijhoff Publishers: Dordrecht, Netherlands, 1986; Brunner H., *Synthesis*, 1988:645; Scheffold R., ed. *Modern Synthetic Methods*, Springer-Verlag: Berlin Hedelberg, 1989;115(5); Nugent W. A., RajanBabu T. V., Burk M. J., *Science*, 1993;259:479; Ojima I., ed. *Catalytic Asymmetric Synthesis*, VCH: New York, 1993; Noyori R., *Asymmetric Catalysis In Organic Synthesis*, New York: John Wiley & Sons, Inc., 1994).

Chiral phosphine ligands have played a significant role in the development of novel transition metal catalyzed asymmetric reactions to produce enantiomeric excess of compounds with desired activities. The first successful attempts at asymmetric hydrogenation of enamide substrates were accomplished in the late 1970's using chiral bisphosphines as transition metal ligands (Vineyard B. D., Knowles W. S., Sabacky M. J., Bachman G. L., Weinkauff D. J., *J. Am. Chem. Soc.*, 1977;99(18):5946–5952; Knowles W. S., Sabacky M. J., Vineyard B. D., Weinkauff D. J., *J. Am. Chem. Soc.*, 1975;97(9):2567–2568).

Since these first published reports, there has been an explosion of research geared toward the synthesis of new chiral bisphosphine ligands for asymmetric hydrogenations and other chiral catalytic transformations (Ojima I., ed. *Catalytic Asymmetric Synthesis*, VCH Publishers, Inc., 1993; Ager D. J., ed. *Handbook of Chiral Chemicals*, Marcel Dekker, Inc., 1999). Highly selective rigid chiral phospholane ligands have been used to facilitate these asymmetric reactions. For example, phospholane ligands are used in the asymmetric hydrogenation of enamide substrates and other chiral catalytic transformations.

BPE, Duphos, and BisP ligands are some of the most efficient and broadly useful ligands developed for asymmetric hydrogenation to date. Burk M. J., *Chemtracts* 11(11), 787–802 (CODEN: CHEMFW ISSN:1431–9268. CAN 130:38423; AN 1998:698087 CAPLUS) 1998; Burk M. J., Bienewald F., Harris M., Zanotti-Gerosa A., *Angew. Chem., Int. ed.*, 1998;37(13/14):1931–1933; Burk M. J., Casy G. Johnson N. B., *J. Org. Chem.*, 1998;63(18):6084–6085; Burk M. J., Kalberg C. S., Pizzano A., *J. Am. Chem. Soc.*, 1998;120(18):4345–4353; Burk M. J., Harper T. G. P., Kalberg C. S.,*J. Am. Chem. Soc.*, 1995;117(15):4423–4424; Burk M. J., Feaster J. E., Nugent W. A., Harlow R. L.,*J. Am. Chem. Soc.*, 1993;1 15(22):10125–10138; Nugent W. A., RajanBabu T. V., Burk M. J., *Science* (Washington, D. C., 1883-) 1993;259(5094):479–483; Burk M. J., Feaster J. E., Harlow R. L., *Tetrahedron: Asymmetry*, 1991;2(7):569–92; Burk M. J., *J. Am. Chem. Soc.*, 1991;113(22):8518–8519; Imamoto T., Watanabe J., Wada Y., Masuda H., Yamada H., Tsuruta H., Matsukawa S., Yamaguchi K., *J. Am. Chem. Soc.*, 1998;120(7):1635–1636; Zhu G., Cao P., Jiang Q., Zhang X.,*J. Am. Chem. Soc.*, 1997;119(7): 1799–1800. For example, a Rhodium/Duphos complex can be used to selectively form (S)-(+)-3-(aminomethyl)-5-methylhexanoic acid, known as pregabalin, which is used as an anti-seizure drug. The S-enantiomer, which is produced in an enantiomeric excess, is preferred because it shows better anticonvulsant activity than the R-enantiomer. Yuen et al., *Bioorganic & Medicinal Chemistry Letters*, 1994;4:823.

The success of BPE, DuPhos, and BisP transition metal complexes in asymmetric hydrogenations is derived from many factors. For example, substrate to catalyst ratios of up to 50,000/1 have been demonstrated. Also, high rates of substrate conversion to product using low hydrogen pressures have been observed with catalysts made from these ligands.

BPE, Duphos, and BisP have shown high enantioselectivities in numerous asymmetric reactions. Improved reaction of BPE, Duphos, and BisP is attributed to, among other factors, rigidity in their $C_2$-symmetric structure. If the spatial area of a metal/phosphine ligand structure, such as BPE, is divided into four quadrants, as shown in Scheme 1, alternating hindered and unhindered quadrants are formed.

Scheme 1

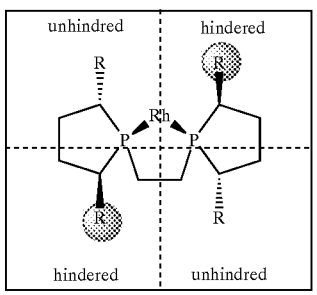

This structural feature creates areas of hindrance in the metal complexes and produces desired stereochemical results in asymmetric hydrogenation reactions. However, there are a variety of reactions, such as catalysis of simple olefins, in which these ligands are not very efficient in terms of activity and selectivity.

Further, there are many characteristics associated with these ligands, which may limit their application. For example, the chiral center of these ligands is not directly bonded to the metal center. This may reduce the effectiveness of enantioselectivity in asymmetric reactions because the chirality of the ligands helps direct the stereochemistry during the reaction of a target molecule with the metal/chiral ligand complex. Therefore, bonding a chiral atom closer to the metal center may increase the formation of enantiomeric excesses. Also, bulky substituents in the unhindered regions may limit the availability and reactivity of the metal center to the target molecule.

Improved chiral phosphine ligands are needed that can further improve the production of enantiomerically active forms of compounds through asymmetric catalysis. Thus, there is a need to develop methods for the production of and to synthesize compounds that bond a chiral phosphine atom directly to a metal center and remove prohibitive substituents from the ligand to improve enantioselectivity in asymmetric reactions.

SUMMARY OF THE INVENTION

The present invention provides for P-chiral bisphospholane ligand enantiomers and methods for their preparation. P-chiral bisphospholanes when complexed with a metal, serve as catalysts in asymmetric hydrogenation reactions to facilitate the formation of a desired stereoisomer. A P-chiral bisphospholane compound of the present invention is represented by the structural Formula I:

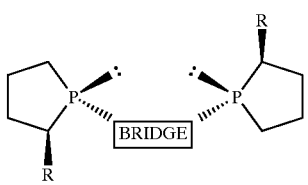

wherein:
R is an alkyl, fluoroalkyl or perfluoroalkyl group each containing up to about 8 carbon atoms, a carboxylic acid group, a carboxylic ester group, an aryl group, a substituted aryl group, an aralkyl group, or a ring substituted aralkyl group; and a Bridge is a —$(CH_2)_n$— where n is an integer from 1 to 12, a 1,2-divalent phenyl, or a 1,2-divalent substituted phenyl. The corresponding enantiomer of Compound I is another compound of the present invention.

Another P-chiral bisphospholane compound of the present invention has the structural Formula VII:

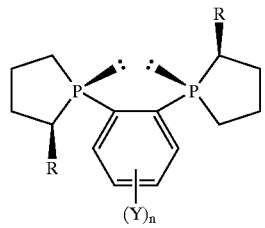

wherein:
R is an alkyl, fluoroalkyl, or perfluoroalkyl group each containing up to about 8 carbon atoms, a carboxylic acid group, a carboxylic ester group, an aryl group, a substituted aryl group, an aralkyl group, or a ring substituted aralkyl group; and each Y is independently halogen, alkyl, alkoxy, aryl, aryloxy, nitro, amino, vinyl, substituted vinyl, alkynyl, or sulfonic acid, and n is an integer from 0 to 4 equal to the number of unsubstituted aromatic ring carbons. The corresponding enantiomer of general Compound VII is another compound of the present invention.

Compounds formed during the synthesis of P-chiral bisphospholane ligands include compounds with the structural Formulae V and VIa and their corresponding enantiomers:

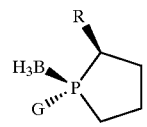

wherein:
R is an alkyl, fluoroalkyl, or perfluoroalkyl group each containing up to about 8 carbon atoms, a carboxylic acid group, a carboxylic ester group, an aryl group, a substituted aryl group, an aralkyl group, or a ring substituted aralkyl group; and G is an alkyl group containing up to about 12 carbon atoms, $NR'_2$, OR', SR', or $SiMe_3$, wherein R' is hydrogen, an alkyl, aryl, substituted aryl, an aralkyl group; or a ring substituted aralkyl group.

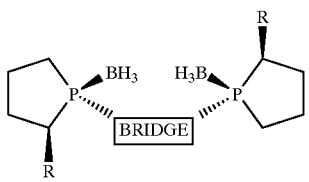

wherein:
R is an alkyl, fluoroalkyl, or perfluoroalkyl group each containing up to about 8 carbon atoms, a carboxylic acid group, a carboxylic ester group, an aryl group, a substituted aryl group, an aralkyl group, or a ring substituted aralkyl group; and a Bridge is a —(CH$_2$)$_n$— where n is an integer from 1 to 12, a 1,2-divalent phenyl, or a 1,2-divalent substituted phenyl.

Other intermediates formed in alternative synthetic routes to P-chiral phospholanes are compounds with the structural Formulae Vb and VIb:

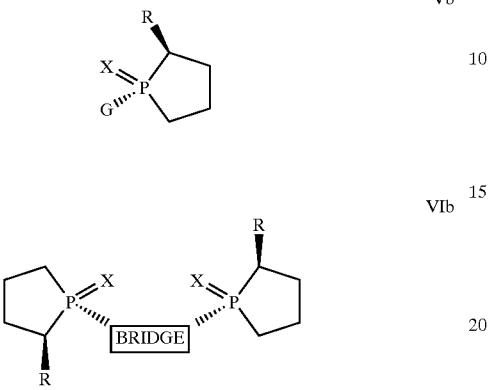

Vb

VIb wherein:

R is an alkyl, fluoroalkyl, or perfluoroalkyl group each containing up to about 8 carbon atoms, a carboxylic acid group, a carboxylic ester group, an aryl group, a substituted aryl group, an aralkyl group, or a ring substituted aralkyl group;

G is an alkyl group containing up to about 12 carbon atoms; NR'$_2$, OR', SR', or SiMe$_3$, wherein R' is hydrogen, an alkyl, aryl, substituted aryl, an aralkyl group; or a ring substituted aralkyl group;

X is S or O; and a Bridge is a —(CH$_2$)$_n$— where n is an integer from 1 to 12, a 1,2-divalent phenyl, or a 1,2-divalent substituted phenyl.

Another aspect of the invention is directed to methods for forming P-chiral bispholane ligands. The methods include preparing a compound of Formula I through several intermediates, as shown in Schemes 3 and 4. One method, for example, includes steps of reacting a bulky alkoxy compound, such as (−)-menthol, with phosphorous trichloride to form a first intermediate of the Formula IIa. The first intermediate is reacted with a divalent alkyl di-Grignard solution and a borane methyl sulfide complex to form a second intermediate with, for example, the Formula IIIa. The second intermediate is then reacted with a chiral base, for example, s-butyl lithium/(−)-sparteine, and an electrophile for enantioselective alkylation of the second intermediate to form a third intermediate, such as IVa. The third intermediate is reacted with methyl anion, such as methyl lithium, to form a fourth intermediate with, for example, the structural Formula Va. The fourth intermediate is then reacted with an oxidative coupling agent to form a fifth intermediate, such as VIa. Compound VIa can be reacted with a borane removing mixture, as depicted n Scheme 4, to form a compound with the structural Formula I or its corresponding enantiomer.

Another aspect of the invention is directed to methods for forming P-chiral bispholane ligand intermediates, such as a compound of Formula 17, through the use of intermediate compounds shown in Schemes 12 and 13.

Another aspect of the invention is directed to methods for forming P-chiral bispholane ligands, such as a compound of Formula I through the use of intermediate compounds shown in Schemes 9 and 10.

Another aspect of the invention is directed to methods for forming a compound of the Formula VII through intermediate compounds, as depicted in Scheme 6. For example, a bis(primary phosphine) is reacted in the presence of a strong base with a cyclic sulfate compound to form a first compound that is then reacted with a chiral base and electrophile for enantioselective alkylation of the first compound to form a second compound. The second compound is reacted with a borane removing mixture to form a compound of the Formula VII or its corresponding enantiomer.

Another compound of the present invention has the structural Formula IX:

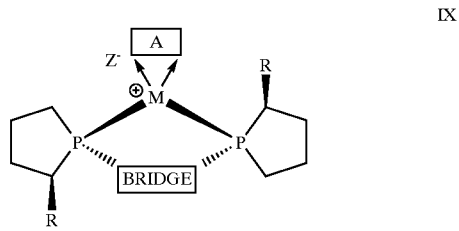

IX wherein:

R is an alkyl, fluoroalkyl, or perfluoroalkyl group each containing up to about 8 carbon atoms, a carboxylic acid group, a carboxylic ester group, an aryl group, a substituted aryl group, an aralkyl group, or a ring substituted aralkyl group;

a Bridge is a —(CH$_2$)n- where n is an integer from 1 to 12, a 1,2-divalent phenyl, or a 1,2-divalent substituted phenyl;

M is a transition metal, an actinide, or a lanthanide;

Z is BF$_4$, PF$_6$, SbF$_6$, OTf, or ClO$_4$; and

A is norbornadiene or cyclooctadiene.

The corresponding enantiomer of general Compound IX is another compound of the present invention.

Another aspect of the invention is directed to methods for forming compounds of the Formula IX, such as IXc, as shown, for example, in Scheme 11.

Yet another aspect of the invention is directed to forming compounds with high enantiomeric excesses in catalytic asymmetric transformations using metal/P-chiral bispholane complexes of the structural Formula IX.

DESCRIPTION OF THE INVENTION

The present invention is related to the synthesis of P-chiral bisphospholane ligands for preparing metal/P-chiral bisphospholane complexes for asymmetric catalysis. In this application, "P-chiral" means that the phosphorous atom or atoms of a compound are chiral centers of that compound. In particular, the present invention is directed to reacting the metal/P-chiral bisphospholane complexes with, for example, acrylates, in asymmetric hydrogenation syntheses to produce enantiomeric excesses of compounds. While the present invention is not so limited, an appreciation of various aspects of the invention will be gained through a discussion of the examples provided below.

For the purpose of this application, the "corresponding enantiomer" means that if a compound includes two P-chiral centers and two C-chiral or chiral carbon atom centers, the "corresponding enantiomer" for a compound having an 1R,2S configuration is the 1S,2R compound. Similarly, if a compound has an 1S,2R configuration, the "corresponding enantiomer" is the 1R,2S compound. If a P-chiral compound has an 1S,2S configuration, the "corresponding enantiomer"

is the 1R,2R compound. If a P-chiral compound has an 1R,2R configuration, the "corresponding enantiomer" is the 1S,2S compound. Phosphorous chiral centers are designated as 1 and carbon chiral centers are designated as 2 in bisphospholanes.

For the purpose of this application, a "compound with a high degree of enantiomeric purity," a "compound of high enantiomeric purity," or a "high level of enantioselectivity" means a hydrogenation that yields a product of greater than or equal to about 80 percent enantiomeric excess (abbreviated e.e.).

Enantiomeric excess is defined as the ratio (% R−% S)/(% R+% S)*100, where % R is the percentage of R enantiomer and % S is the percentage of S-enantiomer in a sample of optically active compound.

P-Chiral Phospholanes

The present invention provides novel P-chiral bisphospholane substituted compounds of the structural Formula I and its corresponding enantiomer:

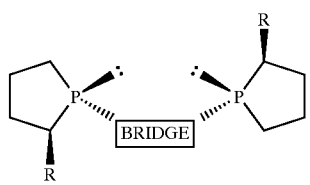

I wherein:
R is an alkyl, fluoroalkyl, or perfluoroalkyl group each containing up to about 8 carbon atoms, a carboxylic acid group, a carboxylic ester group, an aryl group, a substituted aryl group, an aralkyl group, or a ring substituted aralkyl group; and
a Bridge is a —$(CH_2)_n$— where n is an integer from 1 to 12, a 1,2-divalent phenyl, or a 1,2-divalent substituted phenyl.

The term "alkyl," as used in this application includes a straight or branched saturated aliphatic hydrocarbon chain, or cyclic saturated aliphatic hydrocarbons, such as, for example, methyl, ethyl, propyl, isopropyl (1-methylethyl), butyl, tert-butyl (1,1-dimethylethyl), cyclohexyl, cyclopentyl, cyclobutyl, and the like.

The term "fluoroalkyl," as used in this application includes an alkyl, wherein alkyl is defined above, having one or more hydrogen atoms substituted by fluorine atoms.

The term "perfluoroalkyl," as used in this application, includes an alkyl, wherein alkyl is defined above, having all hydrogen atoms substituted by fluorine atoms.

The term "aryl" group, as used in this application, includes an aromatic hydrocarbon group, including fused aromatic rings, such as, for example, phenyl and naphthyl. Such groups may be unsubstituted or independently substituted on the aromatic ring by, for example, halogen, alkyl, alkoxy, aryl, aryloxy, nitro, amino, vinyl, substituted vinyl, alkynyl, or sulfonic acid.

The term "aralkyl" group, as used in this application, includes one or more aryl groups, as defined above, bonded to an alkyl group, for example, benzyl, with the alkyl bonded to the phospholane ring. The aromatic hydrocarbon group may be unsubstituted or substituted (ring substituted aralkyl) by, for example, an alkoxy group of 0 to 4 carbon atoms, an amino group, a hydroxy group, or an acetyloxy group.

The term "substituted phenyl," as used in this application, includes a phenyl group with the unsubstituted aromatic ring carbons independently substituted by, for example, halogen, alkyl, alkoxy, aryl, aryloxy, nitro, amino, vinyl, substituted vinyl, alkynyl, or sulfonic acid.

The term "carboxylic ester," as used in this application, includes a COO group bonded through one oxygen atom to an alkyl, an aryl, or a substituted aryl, wherein alkyl, aryl, and substituted aryl are described above, and the carbon atom bonded to the phospholane ring.

The term "phospholane ring," as used in this application, includes a 5-membered cyclic structure in which at least one atom is phosphorous.

The term "transition metal," as used in this application, includes scandium, titanium, vanadium, chromium, manganese, iron, cobalt, nickel, copper, yttrium, zirconium, niobium, molybdenum, technetium, ruthenium, rhodium, palladium, silver, lanthanum, hafnium, tantalum, tungsten, rhenium, osmium, iridium, platinum, and gold.

The term "actinide," as used in this application includes thorium, protactinium, uranium, neptunium, plutonium, americium, curium, berkelium, californium, einsteinium, fermium, mendelevium, nobelium, and lawrencium.

The term "lanthanide," as used in this application includes cerium, praseodymium, neodymium, promethium, samarium, europium, gadolinium, terbium, dysprosium, holmium, erbium, thulium, ytterbium, and lutetium.

The bisphospholane compounds of Formula I are disubstituted with an R group bonded to one of the carbons of the phospholane ring and a bridging group bonded between the phosphorus on the phospholane rings. The compounds lack an R group in the unhindered quadrant of the phospholane ring, as shown in Scheme 2.

Scheme 2

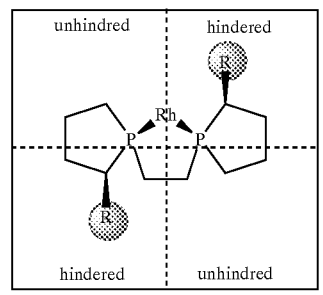

The P-chiral bisphospholane locates chirality closer to the metal center than in known metal/phospholane complexes, such as Duphos and BisP. The chiral center's closer proximity to the metal may produce greater enantioselectivity in the end-products. Also, the lack of substituents in the unhindered quadrants of Formula I compounds may improve the availability of the metal center for catalysis.

Typical R groups include, but are not limited to, for example, lower alkyl groups such as methyl, ethyl, and isopropyl, along with bulkier groups such as benzhydryl, fluorenyl, and trityl groups. One typical R group for compounds of Formula I are aralkyl groups, such as a benzyl group. Examples of other P-chiral bisphospholane ligands include, but are not limited to, 1,2-bis((1S,2S)-2-benzylphospholano)-ethane, 1,2-bis((1R,2R)-2-benzylphospholano)-ethane, 1,2-bis((1S,2R)-2-methylphospholano)-ethane, 1,2-bis((1S,2R)-2-ethylphospholano)-ethane. Examples of enantiomers of the P-chiral phospholane ligands of I include, but are not limited to, 1,2-bis((1R,2S)-2-methylphospholano)-ethane, and 1,2-bis((1R,2S)-2-ethylphospholano)-ethane.

The P-chiral bisphospholane substituted compound, 1,2-bis((1R,2R)-2-benzylphospholano)-ethane, is represented by the Formula Ia:

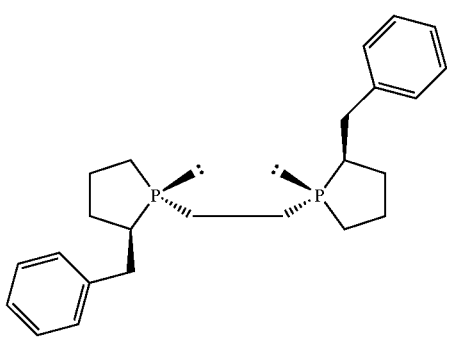

The P-chiral bispholphane substituted compound, 1,2-bis((1S,2S)-2-benzylphospholano)-ethane, is represented by the Formula Ib:

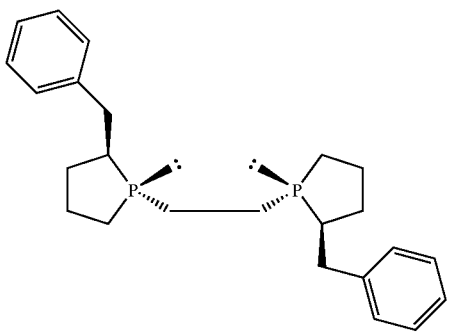

The bisphospholane ligands of the structural Formula I are capable of reacting with transition metals, actinides, or lanthanides to form complexes for use in asymmetric catalysis. The use of these compounds as ligands for transition metals results in catalysts that yield a high level of enantioselective and stereochemical control in the catalyzed hydrogenation of unsaturated substrates.

Several intermediates are formed during the synthesis of compounds of the Formula I. This invention includes intermediate compounds of the formulae V and VIa and their corresponding enantiomers:

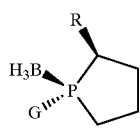

wherein:

R is an alkyl, fluoroalkyl, or perfluoroalkyl group each containing up to about 8 carbon atoms, a carboxylic acid group, a carboxylic ester group, an aryl group, a substituted aryl group, an aralkyl group, or a ring substituted aralkyl group; and G is an alkyl group containing up to about 12 carbon atoms, NR'$_2$, OR', SR', or SiMe$_3$, wherein R' is hydrogen, an alkyl, aryl, substituted aryl, an aralkyl group; or a ring substituted aralkyl group.

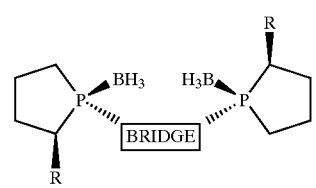

R is an alkyl, fluoroalkyl, or perfluoroalkyl group each containing up to about 8 carbon atoms, a carboxylic acid group, a carboxylic ester group, an aryl group, a substituted aryl group, an aralkyl group, or a ring substituted aralkyl group; and a Bridge is a —(CH$_2$)n- where n is an integer from 1 to 12, a 1,2-divalent phenyl, or a 1,2-divalent substituted phenyl.

Chiral ligands of the structural Formula I can alternatively be prepared through intermediates with the structural formulae Vb and VIb:

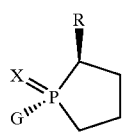

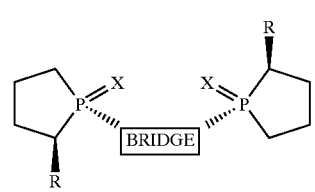

wherein:

R is an alkyl, fluoroalkyl, or perfluoroalkyl group each containing up to about 8 carbon atoms, a carboxylic acid group, a carboxylic ester group, an aryl group, a substituted aryl group, an aralkyl group, or a ring substituted aralkyl group;

G is an alkyl group containing up to about 12 carbon atoms, NR'$_2$, OR', SR', or SiMe$_3$, wherein R' is hydrogen, an alkyl, aryl, substituted aryl, an aralkyl group; or a ring substituted aralkyl group;

X is S or O; and a Bridge is a —(CH$_2$)n- where n is an integer from 1 to 12, a 1,2-divalent phenyl, or a 1,2-divalent substituted phenyl.

Another compound of the present invention has the structural Formula VII:

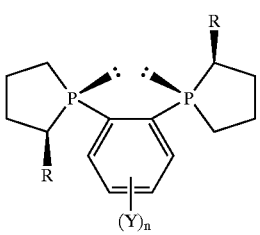

wherein:

R is an alkyl, fluoroalkyl, or perfluoroalkyl group each containing up to about 8 carbon atoms, a carboxylic acid group, a carboxylic ester group, an aryl group, a substituted aryl group, an aralkyl group, or a ring substituted aralkyl group; and each Y is independently halogen, alkyl, alkoxy, aryl, aryloxy, nitro, amino, vinyl, substituted vinyl, alkynyl, or sulfonic acid and n is an integer from 0 to 4 equal to the number of unsubstituted aromatic ring carbons.

The above bisphospholane compounds of Formulae I and VII and their corresponding enantiomers can be complexed with any of the transition metals as well as the lanthanides and actinides. Such complexes are formed by methods known in the art.

Another compound of the present invention includes the metal/P-chiral phospholane complex with the structural Formula IX and its corresponding enantiomer:

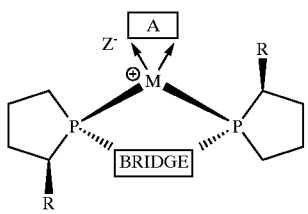

wherein:
R is an alkyl, fluoroalkyl, or perfluoroalkyl group each containing up to about 8 carbon atoms, a carboxylic acid group, a carboxylic ester group, an aryl group, a substituted aryl group, an aralkyl group, or a ring substituted aralkyl group;

a Bridge is a —(CH$_2$)n- where n is an integer from 1 to 12, a 1,2-divalent phenyl, or a 1,2-divalent substituted phenyl;

M is a transition metal, an actinide, or a lanthanide;

Z is BF$_4$, PF$_6$, SbF$_6$, OTf, or ClO$_4$; and

A is norbornadiene or cyclooctadiene.

Z can also be any other appropriate counterion. The anion OTf– is triflate.

Typically useful transition metal complexes of the present invention are those including the above described compounds complexed with rhodium.

Synthesis of Borane-Protected Bisphospholanes

Chiral ligands of the structural Formula I can be prepared as shown in Schemes 3 and 4.

Scheme 3

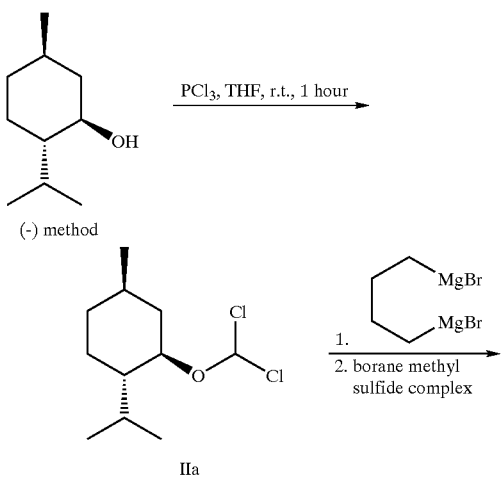

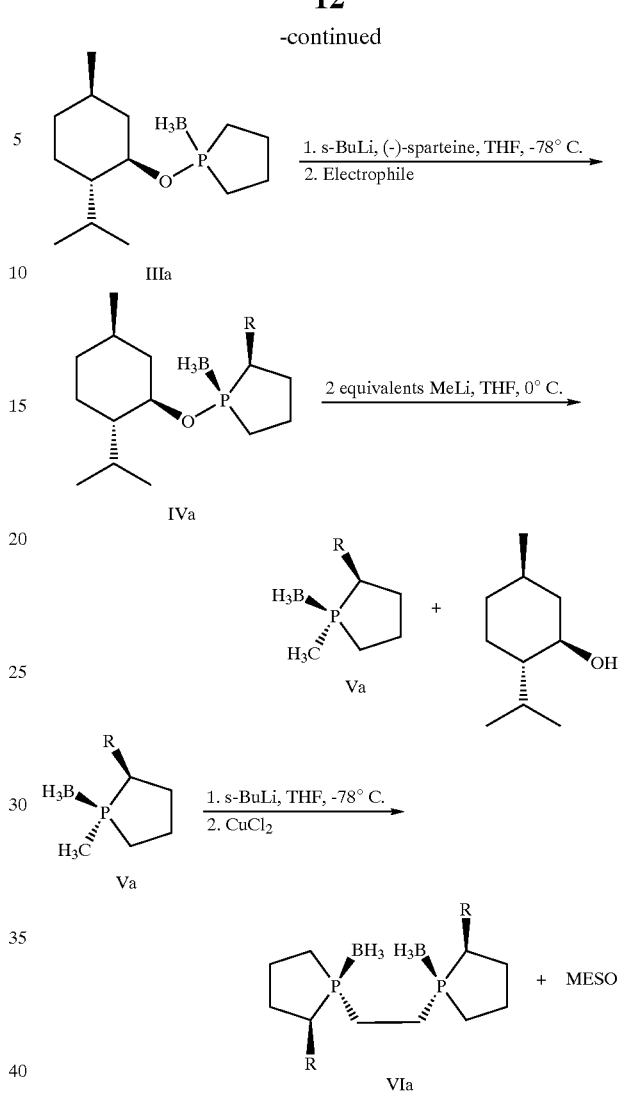

Scheme 4

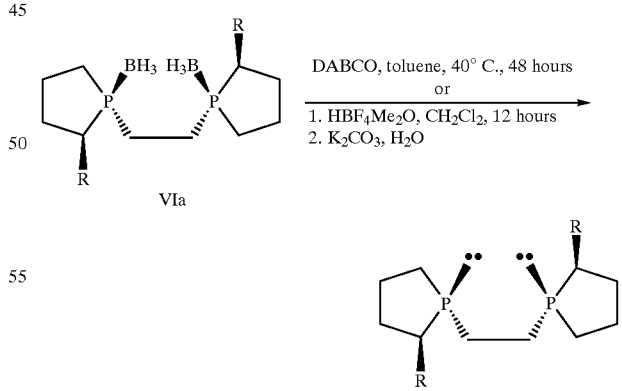

The synthesis route to one of the borane-protected bisphospholane of the Formula VIa is shown in Scheme 3. A chiral menthoxy group is used in this synthesis. The chirality of the menthoxy group is not required in the synthesis, and different alkoxy substituents (chiral and achiral) can be used to accomplish the synthesis of the compounds of the Formula I. For example, an alcohol of the formula R₁OH wherein R₁ is a branched alkyl, an aryl group, a substituted aryl group, an aralkyl group, a ring substituted aralkyl group or other bulky group. For example, adamantyl and phenyl are suitable R₁ substituents. Reaction of (−)-menthol with phosphorous trichloride in tetrahydrofuran produces (−)-menthoxyphosphorous dichloride, shown with the structural Formula IIa in Scheme 3. (+)-Menthol is also suitable for this reaction. An example of an alternative compound for reacting with (−)-menthol includes PBr₃. A phosphine-borane compound of the Formula IIIa, can be formed by reacting (−)-menthoxyphosphorous dichloride with a divalent alkyl di-Grignard solution, shown in Scheme 3, and then a borane complex. Examples of borane complexes include, but are not limited to, a borane methylsulfide complex or alternatively a borane tetrahydrofuran complex, which are commercially available from Aldrich Chemical Co.

The enantioselective alkylation of the phosphine-borane Compound IIIa is performed using a chiral base formed from s-BuLi and (−)-sparteine (Imamoto T., Watanabe J., Wada Y., Masuda H., Yamada H., Tsuruta H., Matsukawa S., Yamaguchi K., *J. Am. Chem. Soc.*, 1998;120(7):1635–1636; Muci A. R., Campos K. R., Evans D. A., *J. Am. Chem. Soc.*, 1995;117(35):9075–9076. Other suitable chiral bases can be used to provide improved enantioselectivities for the chiral alkylation reactions or to form the desired enantiomer, such as compounds having the general formula R₃Li wherein R₃ is an alkyl, an aryl, an alkylamide, or an alkylamine. Compound IVa was synthesized via this chiral alkylation procedure. Selectivity is determined by two factors: the α-carbon atom from which the proton is pulled and the face of the ring at which the resulting anion is alkylated. A proton is pulled selectively from one carbon atom of the phosphine ring using the chiral base. The alkylation occurs selectively on the same side of the ring occupied by the borane group.

The electrophile added for the chiral alkylation can be any electrophile including, but not limited to, an alkyl halide, carbon dioxide, an aldehyde, a ketone, a carboxylic ester, a carbonate, a silyl chloride, or an alkyl sulfonate to form a compound of the Formula IVa as a third intermediate having the group R, wherein R is an alkyl, fluoroalkyl, or perfluoroalkyl group each containing up to about 8 carbon atoms, a carboxylic acid group, a carboxylic ester group, an aryl group, a substituted aryl group, an aralkyl group, or a ring substituted aralkyl group. Examples of suitable electrophiles include, but are not limited to, benzyl bromide, iodomethane, iodoethane, carbon dioxide, chlorotrimethylsilane, benzaldehyde, acetone, cyclopentanone, benzophenone, ethyl acetate, dimethyl carbonate, or di-tert-butyl dicarbonate. The electrophile can be varied to synthesize a variety of ligands that possess different substituents on the phospholane ring to match the steric requirements for producing a specific enantiomer of the target molecules.

The relative stereochemistry of compounds of the structural Formula IVa was assigned by analogy to the crystal structure of the IVa compound wherein R is CO₂H. Apparently, the bulkiness of the menthoxy group blocks the approach of the electrophile from the bottom face of the ring. Therefore, during an alkylation of the bisphospholane, IIIa, without the use of a chiral base, predominantly only 2 diastereomers are formed.

Although the diastereomeric excess of the alkylated products IVa could not be evaluated before displacing the menthoxy group with methyl lithium, the enantiomeric excess of compounds Va could be determined. The values of the enantiomeric excesses ranged from low to mid 70 percent. The relative stereochemistry of Compound Va, wherein R is a benzyl group, was determined via Nuclear Overhauser effect (NOE) studies. The relative stereochemistry of other compounds of the Formula Va, wherein R is either a methyl or an ethyl, was assigned by analogy.

In the synthesis of Compound Va, methyl lithium displaces the menthoxy group with retention of configuration at phosphorous rather than inversion. Other methyl anions can be used to displace the menthoxy group, such as methyl magnesium bromide or methyl cuprate. Had the stereochemistry at phosphorous been inverted, the R groups of Compound I ligands would then reside on the opposite side of the phospholane ring with respect to the lone pairs of electrons on the phosphorous producing the opposite diastereomer. High enantioselectivity would not be expected when using the metal complexes of these ligands in asymmetric hydrogenation were this the case.

The oxidative coupling of Va results in an amplification of the enantiomeric excess of the chiral borane protected product VIa. One oxidative coupling agent reaction includes reacting Va with, for example, s-BuLi and CuCl₂. Alternative oxidative coupling reagents include strong bases, such as s-BuLi in conjunction with various copper(II) salts including, but not limited to CuBr₂, CuI₂, or Cu(OTf)₂, Cu(OPiv)₂. Piv means pivolate. The minor enantiomer of Va reacts predominantly with the major enantiomer to form a meso complex, which can be removed from the reaction mixture by recrystallization. Before work-up of the reaction, Compound VIa exists in less than 100% enantiomeric excess. After recrystallization, VIa is made optically pure. Alternatively, the borane protected ligand of the structural Formula VIa can be synthesized via the route shown in Scheme 5.

Scheme 5

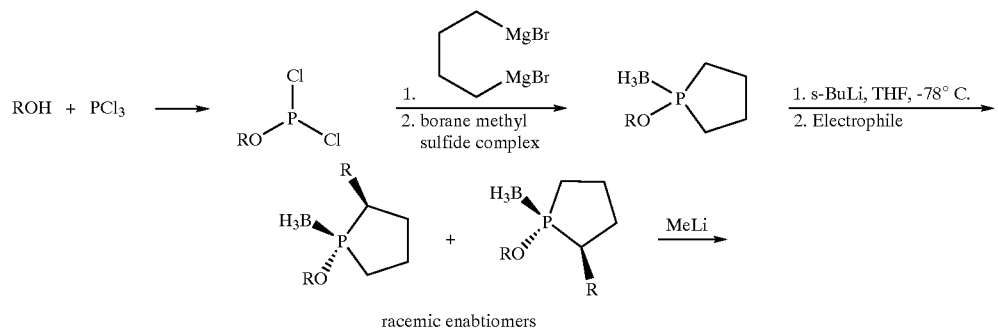

racemic enabtiomers

-continued
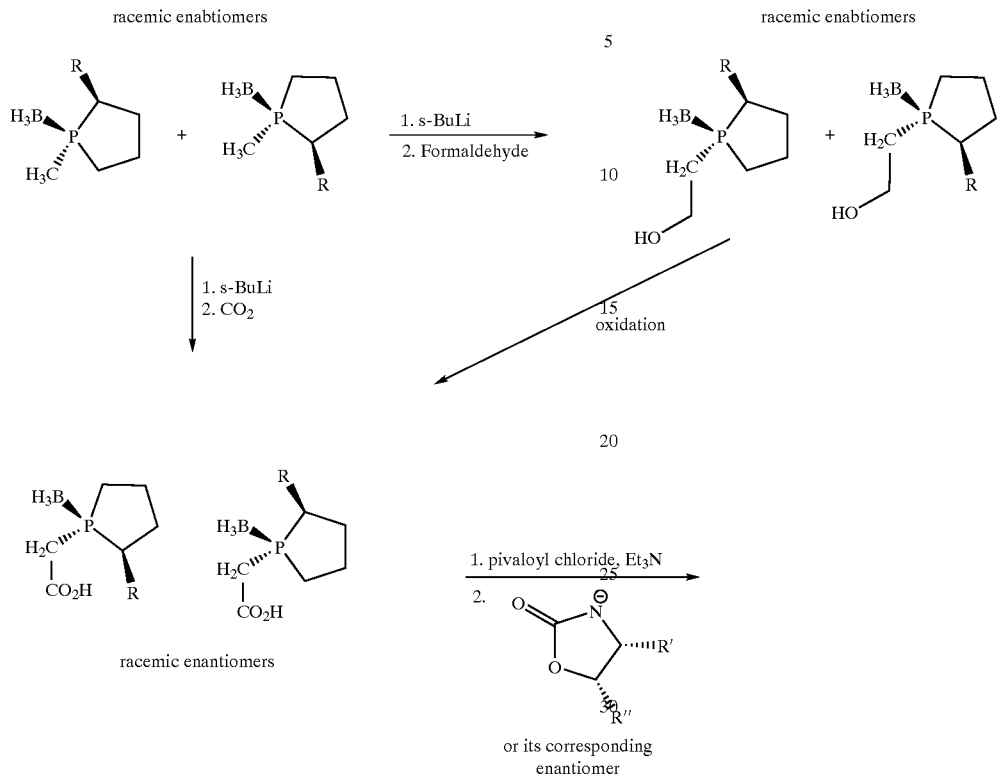
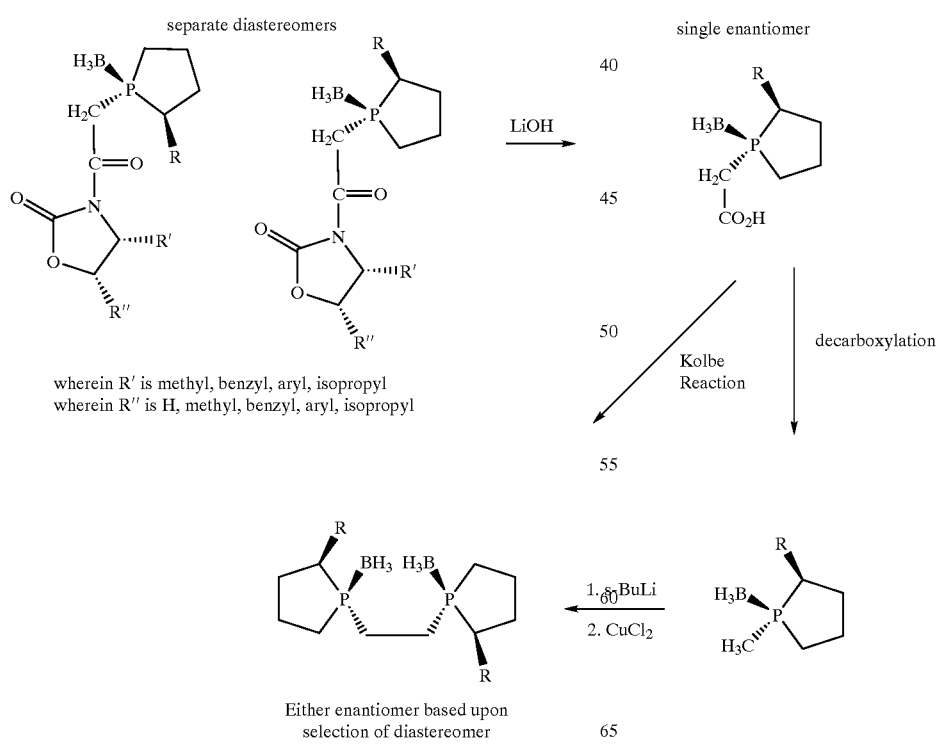

The compound of Formula Xa can be synthesized via the route shown in Scheme 6.

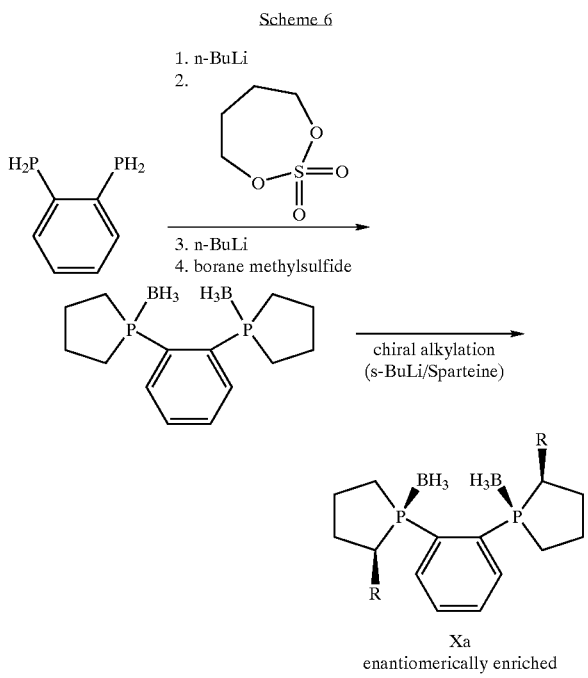

Xa
enantiomerically enriched

As depicted in Scheme 6, a bis(primary phosphine) is reacted with a strong base capable of deprotonating a P—H. For example, 1,2-bis(phosphino)benzene can be reacted with the strong base. Suitable bases include, but are not limited to, sodium amide, potassium hydroxide, sodium hydroxide or compounds with a structural formula $R_3Li$, wherein $R_3$ is an alkyl, an aryl, an alkylamide, or an alkylamine. For example, methyl lithium, n-butyl lithium, phenyl lithium, or lithium diisopropylamide can be used to deprotonate the P—H bond. The strong base removes one proton from the phosphorous atom of each primary phosphine group, forming an anion. The anion is reacted with a cyclic sulfate, shown in Scheme 6, to form a carbon-phosphorous bond on each of the phosphorous atoms. Additional base is then added to remove the remaining proton on each of the phosphorous atoms and a heterocyclic phospholane, a first compound, is formed through a second-carbon-phosphorous bond via sulfate group displacement.

The synthesis of Compound Xa was performed via chiral alkylation. The enantioselective alkylation is performed using a chiral base formed from s-BuLi and (−)-sparteine. Imamoto T., Watanabe J., Wada Y., Masuda H., Yamada H., Tsuruta H., Matsukawa S., Yamaguchi K., *J. Am. Chem. Soc.*, 1998;120(7):1635–1636; Muci A. R., Campos K. R., Evans D. A., *J. Am. Chem. Soc.*, 1995;117(35):9075–6. Alternatively, other suitable chiral bases can be used to provide improved enantioselectivities for the chiral alkylation reactions or to form the desired enantiomer. The electrophile added for the chiral alkylation can be any electrophile including, but not limited to, an alkyl halide, carbon dioxide, an aldehyde, a ketone, a carboxylic ester, a carbonate, a silyl chloride, or an alkyl sulfonate to form a compound with the structural Formula Xa as a second compound having the group R, wherein R is an alkyl, fluoroalkyl or perfluoroalkyl group each containing up to about 8 carbon atoms, a carboxylic acid group, a carboxylic ester group, an aryl group, a substituted aryl group, an aralkyl group, or a ring substituted aralkyl group. Examples of suitable electrophiles include, but are not limited to, benzyl bromide, iodomethane, iodoethane, carbon dioxide, chlorotrimethylsilane, benzaldehyde, acetone, trisylazide, cyclopentanone, benzophenone, ethyl acetate, dimethyl carbonate, or di-tert-butyl dicarbonate. The electrophile can be varied to synthesize a variety of ligands that possess different substituents on the phospholane ring to match the steric requirements for producing a specific enantiomer of the target molecule.

The chiral alkylation step produces an enantiomerically enriched borane protected ligand. If a chiral base is not used in the chiral alkylation step, the borane protected ligand product will have a 1:2:1 ratio of R:meso:S and will not be enantiomerically enriched.

Referring to compounds VIa and Xa, two different borane removing mixtures can be used for borane removal from phosphorous which do not lead to racemization at the P-chiral center, as shown in Scheme 4. Typically, the borane group can be removed by treating the phosphine borane ligand with $HBF_4 \cdot Me_2O$ followed by hydrolysis with $K_2CO_3$. Alternatively, stirring the borane protected ligand, VIa, in toluene with 4 equivalents of DABCO (1,4-diazabicyclo(2.2.2)octane) over 48 hours at 40° C. produces the deprotected ligand of the structural Formula I. Borane removal from Compound IXa results in a compound of the Formula VIIa:

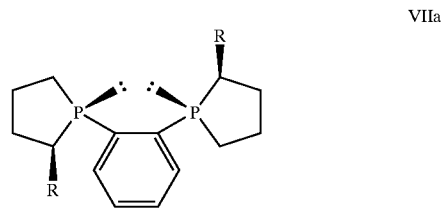

VIIa

Referring to Scheme 7, upon completion of borane removal, the ligand of the structural Formula I was bound immediately to rhodium by reacting the ligand with (Rh (norbornadiene)$BF_4)_2$ to yield a catalyst of Formula IXa.

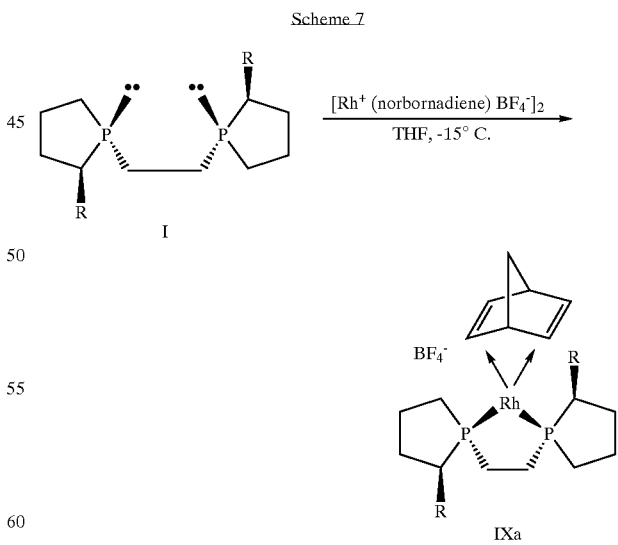

Any suitable transition metal, actinide, or lanthanide and corresponding anion can be used to form the metal/P-chiral phospholane complex shown as Compound IX. For example, the corresponding anion can alternatively be $PF_6^-$, $SbF_6^-$, $OTf^-$, or $ClO_4^-$ or any other appropriate counterion.

As shown in Scheme 8, chiral intermediates Vb and VIb can be formed.

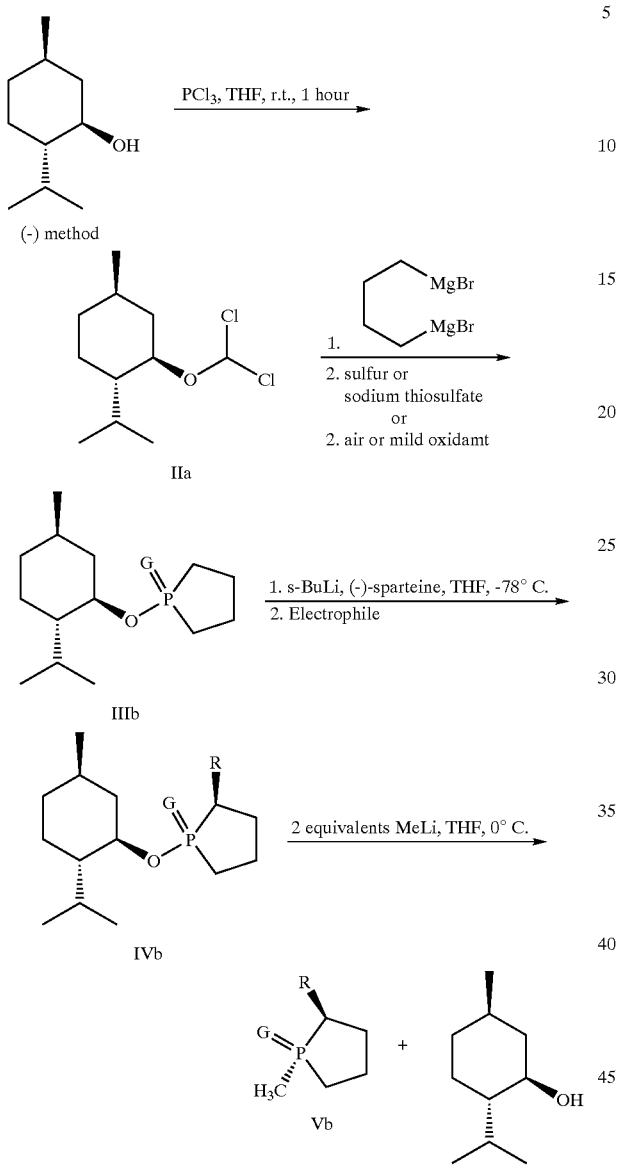

Compound Vb can be oxidatively coupled to produce a compound with the general Formula VIb, wherein the Bridge is —(CH$_2$)$_n$— where n is 2. For example, Vb can be reacted with s-BuLi and CuCl$_2$ to form VIb. Other suitable oxidative coupling agents include, but are not limited to include strong bases, such as s-BuLi in conjunction with various copper(II) salts including, but not limited to CuBr$_2$, CuI$_2$, Cu(OTf)$_2$, or Cu(OPiv)$_2$.

Asymmetric Transformations with Metal\P-Chiral Phospholanes Complexes

Metal/P-chiral phospholane complexes of Formula IX can be used to catalyze hydrogenation and other asymmetric reactions. For example, compounds of Formula IX can be used as catalysts in transformations including, but not limited to, hydrogenation, hydroformylation, π-allyl palladium coupling, hydrosilation, hydrocyanation, olefin metathesis, hydroacylation, and isomerization of allylamines.

For example, a complex represented by the Formula IXc was used to catalyze the substrate, methylacetamidoacetate in the presence of hydrogen, as shown in Scheme 14.

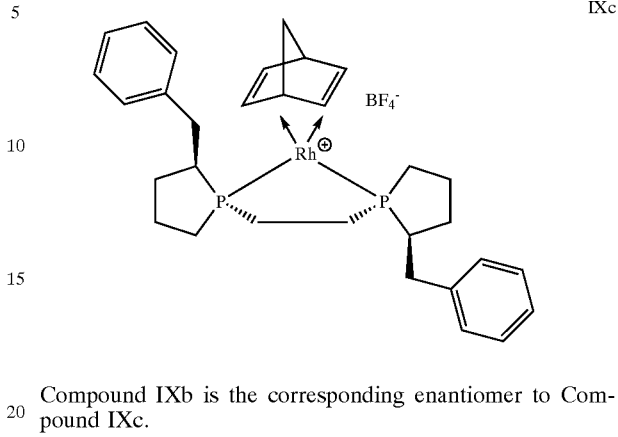

Compound IXb is the corresponding enantiomer to Compound IXc.

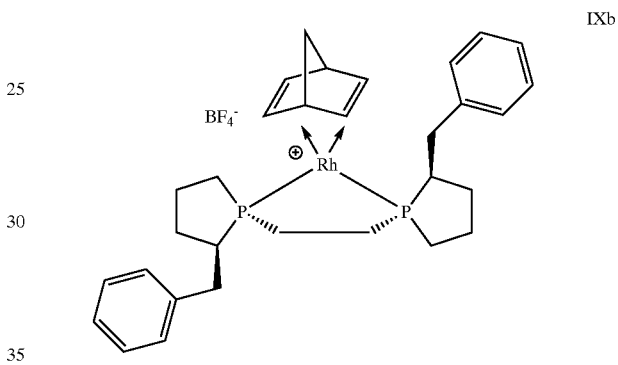

Compounds of the structural Formulas IX, IXb, and IXc typically bond to a substrate to be catalyzed through the center, M, of a compound with the structural Formula IXd, its corresponding enantiomer, or solvates thereof

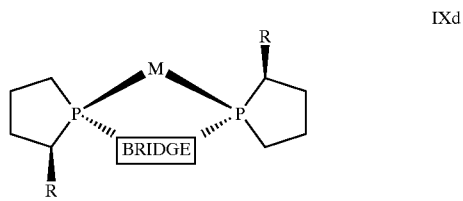

wherein:
R is an alkyl, fluoroalkyl, or perfluoroalkyl group each containing up to about 8 carbon atoms, a carboxylic acid group, a carboxylic ester group, an aryl group, a substituted aryl group, an aralkyl group, or a ring substituted aralkyl group;
a Bridge is a —(CH$_2$)n- where n is an integer from 1 to 12, a 1,2-divalent phenyl, or a 1,2-divalent substituted phenyl; and
M is a transition metal, an actinide, or a lanthanide.

A solvate of the Formula IXc includes compounds having one or more solvent molecules bonded to the M center. The solvent molecules include, but are not limited to, MeOH, THF, ethanol, isopropanol, acetonitrile, methylene chloride, benzene, toluene, water, ethyl acetate, dioxane, carbon tetrachloride, DMSO, DMF, DMF/water mixtures, supercritical carbon dioxide, alcohol/water mixtures, or any other suitable solvent.

Other intermediates can be used to produce a catalyst of the Formula IX that generate either the (S) or (R) enantiomer of the pregabalin precursor. Referring to Scheme 9, either enantiomer of the dimesylate (5) can be synthesized by the choice of (R) or (S) (2,3-epoxypropyl)benzene.

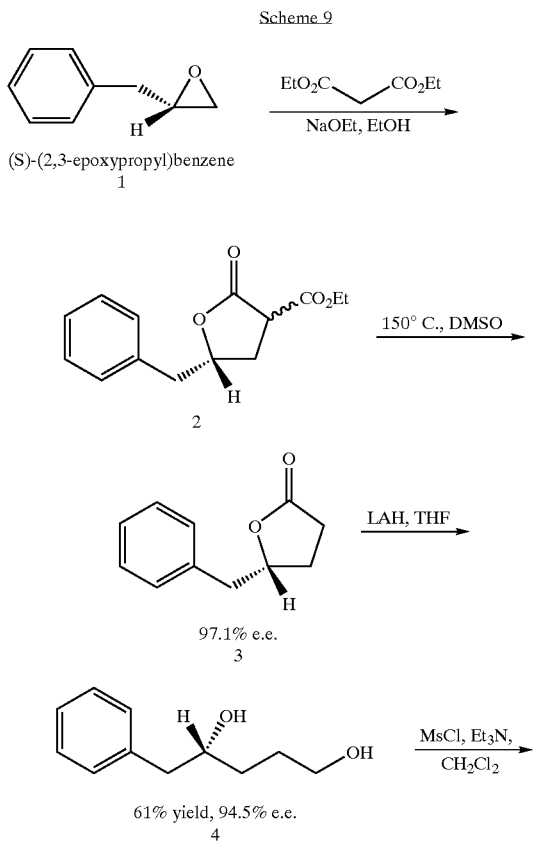

The synthesis shown in Scheme 9 can also be accomplished starting from racemic (2,3-epoxypropyl)benzene (1). The enantiomers of the resulting racemic diol (4) can then be separated on a preparatory scale using chiral HPLC.

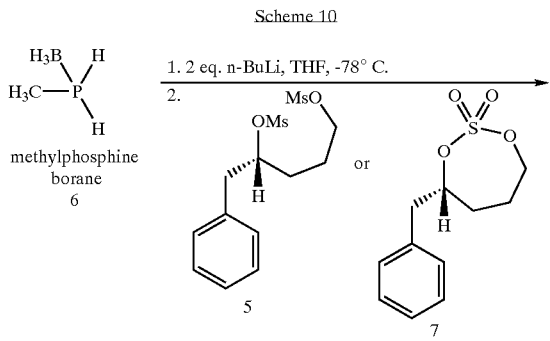

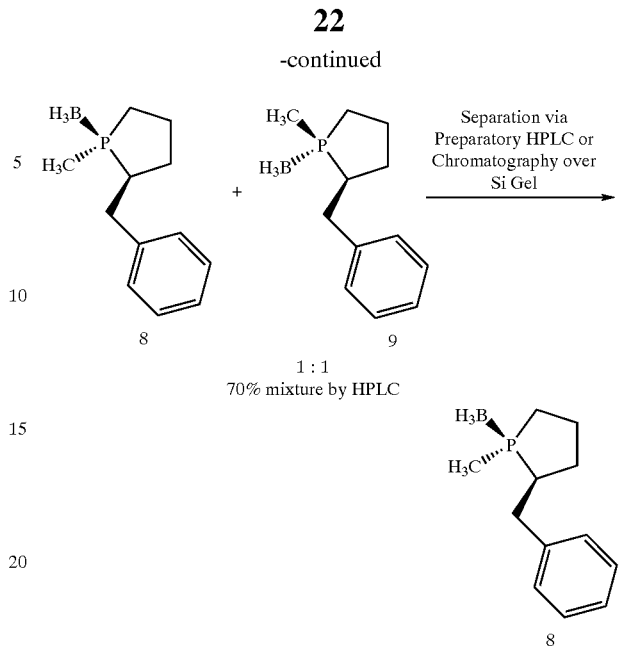

Referring to Scheme 10, methylphosphine borane is reacted with a compound of the Formula (5) or (7) to form compounds of the Formula (8) and (9). The cyclic sulfate (7) can be used in place of the dimesylate (5). The resulting phospholane monomer (8) is a compound of intermediate V. Phospholane monomer (8) can be reacted to form a ligand with the Formula Ib through the same or similar synthetic route as described for Compound Va found in Schemes 3 and 4 and described in Examples 14 and 15. Compound (8) or it corresponding enantiomer can be synthesized based upon the choice of the optically pure dimesylate (5) or cyclic sulfate (7). Compound (9) or its corresponding enantiomer is a diastereomer by-product of the phospholane ring forming reactions in Scheme 10.

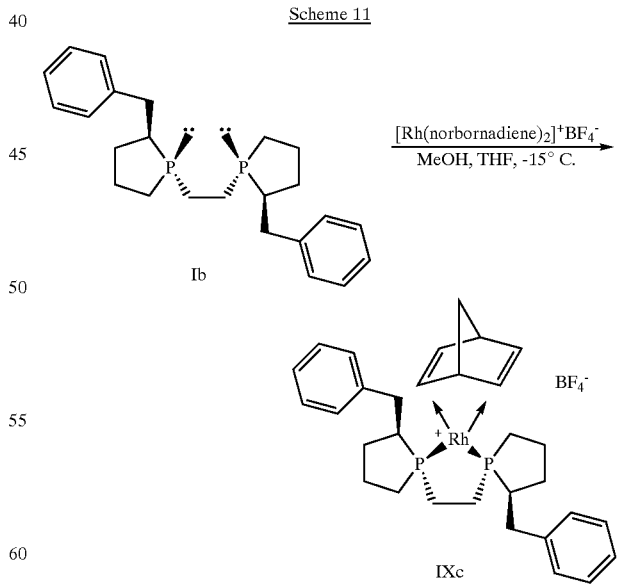

Referring to Scheme 11, Compound Ib dissolved in THF is reacted with [Rh(norbornadiene)$_2$]$^+$ BF$_4^-$ in a solution of MeOH at a temperature of −15° C. The resulting solution was then allowed to warm to room temperature yielding Compound IXc.

Scheme 12

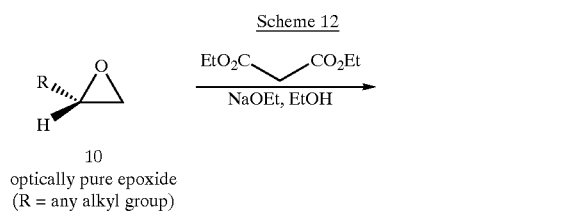

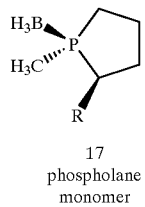

17
phospholane
monomer

Referring to Scheme 13, the synthetic route shown applies to the synthesis of a variety of phospholane monomers (and thus a variety of catalysts) where R is any alkyl group. The cyclic sulfate of Formula (16) can be used in place of the dimesylate of Formula (14). Phospholane monomer (17) corresponds to compounds of the Formula V. Compound (17) or it corresponding enantiomer can be synthesized based upon the choice of the optically pure dimesylate (14) or cyclic sulfate (16). Compound (18) or its corresponding enantiomer is a diastereomer by-product of the phospholane ring forming reactions in Scheme 13. One synthetic route to catalyst IX from phospholane monomers (17) is shown partially in Scheme 3 and in Schemes 4 and 7. Either enantiomer of the catalyst IX can be synthesized based upon the choice of the enantiomer of the dimesylate (14) or cyclic sulfate (16).

Referring to Scheme 12, a synthetic route depicting a general route to a variety of optically pure dimesylates of the Formula (14) where R is any alkyl group is shown. Either enantiomer of these dimesylates can be synthesized based upon the choice of the appropriate enantiomer of the epoxide starting material. Any terminal epoxide can be resolved using Jacobsen epoxide ring opening kinetic resolution catalysts. These optically pure terminal epoxide catalysts are available from Rhodia ChiRex located in Boston, Mass.

Scheme 14

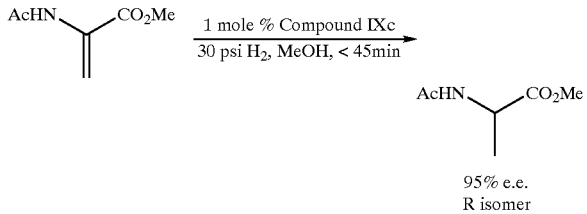

For the reaction shown in Scheme 14, conditions were modified to optimize the hydrogenation of methylacetamidoacetate. One mole percent of ligand IXc in MeOH at 30 psi of hydrogen and at room temperature resulted in enantiomeric excesses on the order of about 95 percent in less than 45 minutes.

The same conditions were used for the hydrogenation of other substrates, shown in Schemes 15 and 16. The substrates of Schemes 15 and 16 were converted quantitatively to their hydrogenation products using these described conditions. Enantiomeric excess for the products were 86 percent in Scheme 15 and 76 percent in Scheme 16 with 100 percent conversion in both reactions.

Scheme 13

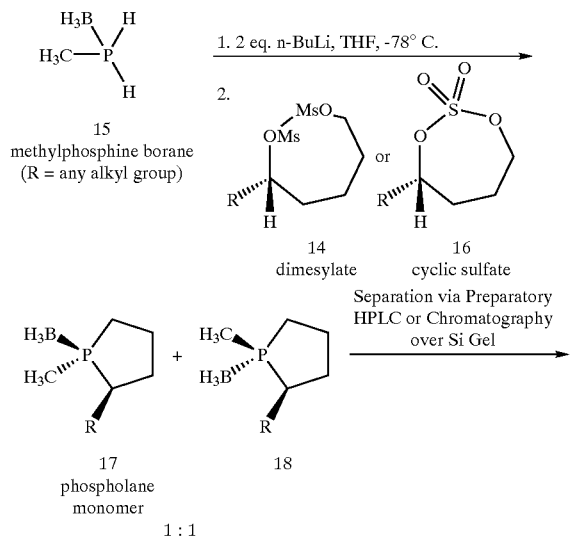

Scheme 15

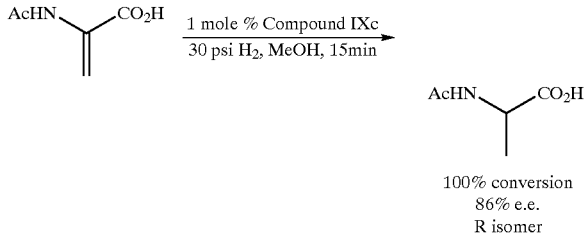

Scheme 16

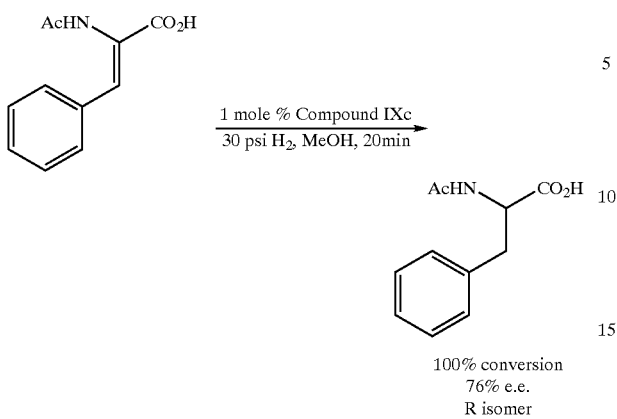

Asymmetric reduction experiments of the potassium salt of 3-cyano-5-methylhex-3-enoic acid have been run using catalyst IXc to produce a pregabalin precursor, as shown in Scheme 17. The t-butylammonium salt of 3-cyano-5-methylhex-3-enoic acid can also be reacted with catalyst IXc to produce the pregabalin precursor. Other substrates that can be reacted with catalyst IXc to undergo asymmetric reduction to produce additional pregabalin precursors are 3-cyano-5-methylhex-3-enoic acid methyl ester and 3-cyano-5-methylhex-3-enoic acid ethyl ester. The pregabalin precursor can then be converted into pregabalin. Pregabalin is the generic name for (S)-(+)-(Aminomethyl)-5-methylhexanoic acid. Pregabalin is used in the treatment and prevention of seizure disorders, pain, and psychotic disorders.

Scheme 17
Asymmetric hydrogenation of the potassium salt of 3-cyano-5-methylhex-3-enoic acid

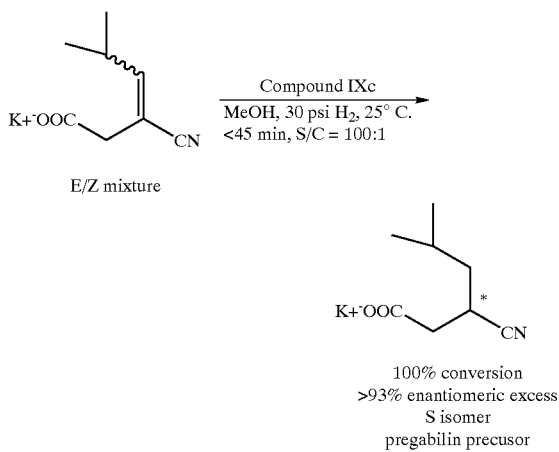

The hydrogenation experiments show high enantiomeric excesses and conversion rates of the substrates. Hydrogenation of E/Z mixtures of the potassium salt of 3-cyano-5-methylhex-3-enoic acid gave greater than 93 percent enantiomeric excess of product. Other salts of 3-cyano-5-methylhex-3-enoic acid can undergo asymmetric hydrogenation, such as the t-butylamine salt or any other salt of the acid.

Enantiomeric excess determination of the products from the reductions of substrates was accomplished by acidifying the hydrogenated reaction mixture and then treating the carboxylic acid product with tms-diazomethane to form the methyl ester. The enantiomeric ratios of the methyl ester were analyzed via chiral gas chromatography (GC). The assignment of the stereochemistry of the enantiomers was done by comparison of elution order of the methyl esters.

Referring to Scheme 18, a general reaction scheme is shown for the conversion of a pregabalin precursor, such as the pregabalin precursor shown in Scheme 17, to pregabalin.

Scheme 18

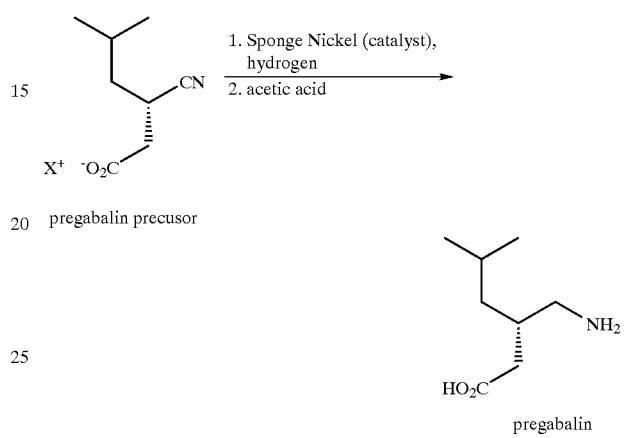

Enantiomerically enriched pregabalin precursor, wherein $X^+$ is $K^+$, $Li^+$, $Na^+$, or t-butylammonium, can be recrystallized to form optically pure material that is converted to pregabalin. The optically pure pregabalin precursor can be converted directly to pregabalin by first hydrogenating the nitrile group with sponge nickel in the presence of hydrogen and then acidifying the resulting mixture with acetic acid.

P-Chiral Ligand and Catalysts

General Procedures and Materials

Materials

THF was either distilled from sodium prior to use or obtained from Aldrich Sure-Seal bottles supplied by Aldrich Chemical Company as 99.9% anhydrous. Dichloromethane (anhydrous, 99.8%) and ether (anhydrous, 99.8%) were used as needed from Aldrich Sure-Seal bottles supplied by Aldrich Chemical Company. (1R,2S,5R)-(−)-Menthol, borane methylsulfide complex (approximately 10–10.2 M), phosphorous trichloride (98%), 1.3M s-BuLi in cyclohexane, (−)-sparteine, benzyl bromide (98%), 1.0M MeLi in THF/cumene, tetrafluoroboric acid-dimethyl ether complex ($HBF_4.Me_2O$), trimethylsilyldiazomethane, methyl 2-acetamidoacrylate, 2-acetamidoacrylic acid, and α-acetamidocinnamic acid were obtained from Aldrich Chemical Company. $AgBF_4$ (99%) and Chloronorbornadiene rhodium (I) dimer (99%) were supplied by Strem Chemicals, Incorporated. Hydrogen gas (99.995%) was used from a lecture bottle supplied by Specialty Gas.

Hydrogenations were performed in a Griffin-Worden pressure vessel supplied by Kimble/Kontes. (S)-(2,3-epoxypropyl)benzene (99.9% chemical purity, 98.2% enantiomeric excess) was purchased from Rhodia-Chirex on a custom synthesis contract. Sodium metal (stick, dry, 99%), diethylmalonate (99%), lithium aluminum hydride (powder, 95%), methanesulfonylchloride (99.5+%), triethylamine (99.5%), n-BuLi (2.5M in hexanes), and s-BuLi (1.3 M in cyclohexane) were purchased from Aldrich Chemical Company. $AgBF_4$ (99%) and Chloronorbornadiene rhodium(I)

dimer (99%) were supplied by Strem Chemicals, Incorporated. Methylphosphine borane was purchased from Digital Chemical Company on a custom synthesis contract.

Nuclear Magnetic Resonance

400 MHz $^1$H NMR, 100 MHz $^{13}$C NMR, and 162 MHz $^{31}$P NMR spectra were obtained on "Barton"—a Varian Unity+400 (Inova400 after Aug. 15, 2000) spectrometer equipped with an Auto Switchable 4-Nuclei PFG probe, two RF channels, and a SMS-100 sample changer by Zymark. Spectra were generally acquired near room temperature (21° C.), and standard autolock, autoshim and autogain routines were employed. Samples are usually spun at 20 Hz for 1D experiments. $^1$H NMR spectra were acquired using 45-degree tip angle pulses, 1.0 second recycle delay, and 16 scans at a resolution of 0.25 Hz/point. The acquisition window was typically 8000 Hz from +18 to −2 ppm (Reference TMS at 0 ppm), and processing was with 0.2 Hz line broadening. Typical acquisition time is 80 seconds. Regular $^{13}$C NMR spectra were acquired using 45° tip angle pulses, 2.0 second recycle delay, and 2048 scans at a resolution of 1 Hz/point. Spectral width was typically 25 KHz from +235 to −15 ppm (Reference TMS at 0 ppm). Proton decoupling was applied continuously, and 2 Hz line broadening was applied during processing. Typical acquisition time is 102 minutes. $^{31}$P NMR spectra were acquired using 45-degree tip angle pulses, 1.0 second recycle delay, and 64 scans at a resolution of 2 Hz/point. Spectral width was typically 48 KHz from +200 to −100 ppm (Reference 85% Phosphoric Acid at 0 ppm). Proton decoupling was applied continuously, and 2 Hz line broadening was applied during processing. Typical acquisition time is 1.5 minutes.

Mass Spectrometry

Mass Spectrometry was performed on a Micromass Platform LC system operating under MassLynx and OpenLynx open access software. The LC was equipped with a HP1100 quaternary LC system and a Gilson 215 liquid handler as an autosampler. Data was acquired under atmospheric pressure chemical ionization with 80:20 acetonitrile/water as the solvent. Temperatures: probe was 450° C., source was 150° C. Corona discharge was 3500V for positive ion and 3200V for negative ion.

High Performance Liquid Chromatography

High Performance Liquid Chromatography (HPLC) was performed on a series 1100 Hewlett Packard (now Agilent Technologies) instrument equipped with a manual injector, quaternary pump, and a UV detector. The LC was PC controlled using HP Chemstation Plus Software. Reverse phase HPLC was performed with a 150×4.6 mm BDS-Hypersil-C18 column supplied by Keystone Scientific Incorporated. Reverse phase chiral HPLC was performed using a Chiracel OJ-R column supplied by Chiral Technologies. Normal Phase chiral HPLC was performed using Chiracel OJ, Chiracel OD, Chiracel OD-H, Chiracel AD, and Chiracel AS columns supplied by Chiral Technologies.

Gas Chromatography. Gas Chromatography (GC) was performed on a 110 volt Varian Star 3400 equipped with an FID detector with electrometer, a model 1061 packed/530 micron ID flash injector, a model 1077 split/splitless capillary injector, a relay board that monitors four external events, and an inboard printer/plotter. Gas chromatography was performed using 40 m×0.25 mm Chiraldex G-TA or B-TA columns supplied by Advanced Separation Technologies, Incorporated or a 25 m×0.25 mm Coating CP Chirasil-Dex DB column supplied by Chrompack.

X-Ray Crystallography

X-Ray crystallography was performed on an Enraf Nonius CAD-4 instrument. Cell refinement was done with CAD-4. Data reduction, structure solving, structure refinement, molecular graphics, and preparation of data for publication were done with maXus software.

EXAMPLES

Example 1 (as Depicted in Scheme 3)

Synthesis of (−)-menthoxyphosphorous dichloride

Into a 250 mL round bottom flask was placed (1R, 2S, 5R)-(−)-menthol (12.54 g, 0.0802 mole) under $N_2$. Freshly distilled THF (100 mL) was added via syringe, and the solution was then cooled to 0° C. Into this stirring solution was added $PCl_3$ (7.0 mL, 0.0802 mole) dropwise with stirring over 4 minutes. The reaction was stirred for 1 hour and then the THF was removed on a rotary evaporator working quickly in air to avoid hydrolyzing the product. The colorless crude product was distilled (81° C./0.5 mm Hg) to yield 15.8 g (77%) of (−)-menthoxyphosphorous dichloride. The (−)-menthoxyphosphorous dichloride was kept under $N_2$ at room temperature until needed. $^1$H NMR (400 MHz, $CDCl_3$) δ 0.78 (d, J=7.8 Hz, 3 H), 0.84 (m, 1 H), 0.89 (d, J=7.6 Hz, 3 H), 0.91 (d, J=7.8 Hz, 3 H), 0.98–1.08 (m, 1 H), 1.16–1.25 (m, 1 H), 1.32–1.38 (m, 1 H), 1.41–1.51 (m, 1 H), 1.64–1.70 (m, 2 H), 1.96–2.03 (m, 1 H), 2.32–2.35 (m, 1 H), 4.42–4.52 (m, 1 H); $^{13}$C NMR (100 MHz, $CDCl_3$) δ 83.7 (d, $J_{C-P}$=9.9 Hz), 48.7, 43.3, 33.9, 31.6, 25.1, 22.9, 22.0, 21.2, 16.0; $^{31}$P NMR (162 MHz, $CDCl_3$) δ 176.7.

Example 2 (as Depicted in Scheme 3)

Synthesis of Phosphine-Borane Compound

Into a 3-neck 250 mL round bottom flask equipped with a reflux condenser under $N_2$ was placed 150 mL freshly distilled THF and magnesium (2.36 g, 0.0973 mole). An iodine crystal was added and then 1,4-dibromobutane (4.65 mL, 0.0389 mole) was added dropwise over 30 minutes with a syringe pump while the reaction was stirred with a magnetic stirbar. The reaction became hot during the addition and refluxed near the end of the addition (an ice bath was kept on hand to cool the reaction to prevent it from becoming uncontrollable). After addition, the reaction was refluxed for 1 hour. The divalent alkyl di-Grignard solution (dark gray after reflux) was then cooled to room temperature. Into a separate 500 mL flask was placed the (−)-menthoxyphosphorous dichloride of Example 1 (10.0 g, 0.0389 moles) and 250 mL of freshly distilled THF under $N_2$. The (−)-menthoxyphosphorous dichloride solution was cooled to 0° C. and then the di-Grignard solution was delivered to the flask quickly via cannula. The reaction mixture was warmed to room temperature and then stirred 3 hours whereupon $BH_3.Me_2S$ (3.9 mL of a 10.0 M solution, 0.0389 moles) was delivered to the reaction via syringe and the reaction was stirred overnight (although protection was probably complete in 1 hour). The reaction was quenched cautiously with 250 mL of $H_2O$, the organic layer was separated, and the aqueous layer was extracted with 3×100 mL $Et_2O$. The combined organics were dried over $MgSO_4$ and then the solvent was removed on a rotary evaporator. Column chromatography over silica gel (1% EtOAc/hexane) yielded 5.13 g/52% of a phosphine borane compound (in 2.5% EtOAc/hexane $R_f$ desired product=0.38, $R_f$ unidentified small side products=0.48 and 0.71, all products were visualized on TLC plates with phosphomolybdic acid staining). The phosphine borane compound was kept at 0° C. under $N_2$ in the freezer until use. $^1$H NMR (400 MHz, $CDCl_3$) δ 0.1–1.0 (br m, 3 H), 0.78 (d, J=7.1 Hz, 3 H), 0.87 (d, J=5.4 Hz, 3 H), 0.88 (d, J=4.6 Hz, 3 H), 0.91–1.04 (m, 2 H), 1.17–1.24 (m, 2 H), 1.36–1.48 (m, 1 H), 1.57–1.64 (m, 2 H), 1.89–1.96 (m, 9 H), 2.05–2.08 (m, 1 H), 3.90–3.99 (m, 1 H); $^{13}$C NMR (100 MHz, CDCl$_3$) δ 16.0, 20.9, 22.1, 23.0, 25.4, 25.80, 25.84, 29.1 (d, J$_{C-P}$=42.0 Hz), 30.5 (d, J$_{C-P}$=37.4 Hz), 31.3, 34.2, 43.4, 48.6, 79.0 (d, J$_{C-P}$=3.8 Hz); $^{31}$P NMR (162 MHz, CDCl$_3$) δ 142.

Example 3 (as Depicted in Scheme 3)
Synthesis of (1S,2R)-2-benzyl-1-(−)-menthoxy-phospholane borane The phosphine-borane compound of Example 2 (8.83 g, 0.0345 mole) was placed in a 500 mL round bottom flask and dissolved in 150 mL Et$_2$O at −78° C. under N$_2$. In a separate flask, (−)-sparteine (9.9 mL, 0.043 mole) was placed in a 250 mL flask and dissolved in 100 mL of Et$_2$O under N$_2$. The (−)-sparteine solution was cooled to −78° C. and then s-BuLi (33.2 mL of 1.3 M in cyclohexane solution reagent, 0.043 mole) was added via syringe. The s-BuLi/sparteine solution was then delivered to the flask containing the phosphine-borane compound via cannula at −78° C. over 30 minutes. After addition, the reaction was stirred for 2 hours. In a separate 100 mL flask was dissolved benzyl bromide (5.3 mL, 0.0449 mole), an electrophile, in 50 mL Et$_2$O under N$_2$. The benzyl bromide solution was then delivered quickly to the anion solution via cannula. The cold bath was removed and the reaction was allowed to warm slowly to room temperature. The reaction was then quenched with 500 mL 1N HCl. The organic layer was separated, and then the aqueous layer was extracted with 2×75 mL Et$_2$O. The combined organic layers were dried over MgSO$_4$, and then the solvent was removed on a rotary evaporator. The crude product was chromatographed over silica gel (1.5% EtOAc/hexane) to yield 9.14 g/77% of (1S,2R)-2-benzyl-1-(−)-menthoxy-phospholane borane. Determination of the d.e. of the product was not possible at this stage. $^1$H NMR (400 MHz, CDCl$_3$) δ 0.2–1.1 (m, 14 H), 1.2–1.4 (m, 3 H), 1.3–1.5 (m, 1 H), 1.7–2.0 (m, 8 H), 2.18–2.30 (m, 1 H), 2.20–2.25 (m, 1H), 2.55–2.61 (m, 1 H), 3.15–3.21 (m, 1H), 3.96–4.02 (m, 1 H), 7.15 (m, 3 H), 7.24–7.29 (m, 2 H); $^{13}$C NMR (100 MHz, CDCl$_3$) δ 16.2, 20.9, 22.1, 23.1, 23.7, 26.0, 30.3, 31.2, 31.3, 34.2, 34.9, 43.4, 44.3, 48.7, 79.0 (d, J$_{C-P}$=4.6 Hz), 126.2, 128.5, 128.7, 140.7 (d, 14.5 Hz); $^{31}$P NMR (162 MHz, CDCl$_3$) dd 143.5 (m).

Example 4 (as Depicted in Scheme 3)
Synthesis of (1S,2R)-2-carboxylic acid-1-(−)-menthoxy-phospholane borane The phosphine-borane compound of Example 3 (3.60 g, 14.1 mmole) was placed in a 500-mL round bottom flask and dissolved in 100 mL Et$_2$O at −78° C. under N$_2$. In a separate flask, (−)-sparteine (4.0 mL, 0.0176 mole) was placed in a 250-mL flask and dissolved in 100 mL of Et$_2$O under N$_2$. The (−)-sparteine solution was cooled to −78° C. and then s-BuLi (13.5 mL of 1.3 M in cyclohexane solution reagent, 17.6 mmole) was added via syringe. The s-BuLi/sparteine solution was then delivered to the flask containing the phosphine borane via cannula at −78° C. over 30 minutes. After addition, the reaction was stirred for 2 hours. Carbon dioxide was then bubbled through the solution from a tank for 30 seconds. The cold bath was removed and the reaction was warmed to room temperature. The reaction was quenched with 100 mL of 1N HCl. The organic layer was separated and then the aqueous layer was extracted two times with 75 mL ethyl acetate. The combined organic layers were then dried over MgSO$_4$ and the volatiles were removed invacuo. The white solid product was passed through a silica gel column with a 15% ethyl acetate/hexane solution. The solution was allowed to stand overnight and x-ray quality crystals (colorless plates) grew along the side of the flask during that period.

Example 5 (as Depicted in Scheme 3)
Synthesis of (1S,2R)-2-benzyl-1-methyl-phospholane The substituted phosphine borane compound of Example 4 (9.14 g, 44.37 mmole) was placed in a 250-mL round bottom flask and dissolved in 120 mL of THF under N$_2$. The solution was warmed to 50° C. To the solution was added MeLi (92.4 mL, 1.0 M in THF/cumene solution, 92.4 mmole) via syringe. The solution became yellow after addition and after an hour the solution was light red. The reaction was followed by TLC (2.5% EtOAc/hexane) and was deemed complete at that time. The reaction was quenched carefully with 300 mL 1N HCl and then the organic layer was separated. The aqueous layer was extracted with 2×100 mL Et$_2$O. The combined organic layers were dried over MgSO$_4$ and then the solvent was removed on a rotary evaporator. Column chromatography of the crude product over silica gel (2.5% EtOAc/hexane) yielded 2.83 g/52% of the title compound. Analysis of the product by chiral HPLC (Chiracel OJ-R, 60% CH$_3$CN/40% (5% CH$_3$CN in H$_2$O), 1 mL/min, enantiomers at 4.31 min (major) and 5.02 min (minor); enantiomeric excess could also be analyzed with the following conditions: Chiracel OD-H, 80% hexane/20% isopropanol, 1 mL/min, enantiomers at 5.29 min (minor) and 5.59 min (major)) showed 75% e.e. The assignment of the relative stereochemistry was accomplished by 1-D NMR experiments. $^1$H NMR (400 MHz, CDCl$_3$) δ 0.05–0.97 (br m, 3 H), 1.25 (d, J=10.7 Hz), 1.42–1.70 (m, 2 H), 1.70–2.20 (m, 5 H), 2.64–2.73 (m, 1 H), 3.06–3.13 (m, 1 H), 7.17–7.29 (m, 5 H); $^{13}$C NMR (100 MHz, CDCl$_3$) δ 11.8 (d, Jc-p=31.3 Hz), 24.4, 25.8 (d, Jc-p=37.4 Hz), 25.8, 33.2, 35.4, 41.0 (d, J=33.6 Hz), 41.0, 126.3, 128.5, 128.8, 140.5 (d, Jc-p=11.5 Hz); $^{31}$P (162 MHz, CDCl$_3$) δ 29.4 (m).

Example 6 (as Depicted in Scheme 3)
Synthesis of 1,2-bis((1R,2R)-2-benzylphospholano borane)-ethane The (1S,2R)-2-benzyl-1-methyl-phospholane product of Example 5 (2.83 g, 13.74 mmole) was dissolved in 80 mL THF under N$_2$ and cooled to −78° C. To this solution was added s-BuLi (11.6 mL, 1.3 M cyclohexane solution reagent) via syringe and the solution turned red. After stirring for 2 hours at −78° C., CuCl$_2$ powder was added to the reaction in one portion with vigorous stirring. The reaction was allowed to warm to room temperature with the cold bath and then was stirred overnight. The mixture was quenched with 100 mL conc. NH$_4$OH and the organic layer was separated. The aqueous layer was then extracted with 3×50 mL EtOAc. The combined organic layers were washed with 5% NH$_4$OH, 1N HCl, and brine. The organic layer was then dried over MgSO$_4$ and the solvent removed on a rotary evaporator. The crude product was recrystallized 3 times from hot isopropanol to yield 1.15 g/41% of 1,2-bis((1S,2S)-2-benzylphospholano borane)-ethane. HPLC analysis (Chiralcel OD-H, 80% hexane/20% isopropanol, 0.5 mL/min, enantiomers at 12.81 min and 16.84 min, meso at 14.51 min) showed >99% e.e. of product and >98% purity. $^1$H NMR (400 MHz, CDCl$_3$) δ 0.0–1.0 (m, 6 H), 1.15–1.30 (m, 2 H), 1.40–1.60 (m, 6 H), 1.70–1.80 (m, 4 H), 1.90–2.10 (m, 6 H), 2.68–2.78 (m, 2 H), 2.92–2.99 (m, 2 H), 7.16–7.24 (m, 6 H), 7.27–7.31 (m, 4 H); $^{13}$C NMR (100 MHz, CDCl$_3$) dd 19.9 (d, J$_{C-P}$=26.7 Hz), 24.5, 24.6 (d, J$_{C-P}$=36.6 Hz), 24.8, 33.9, 35.5, 40.4 (d, J=32.0 Hz), 126.5, 128.5, 129.1, 140.3; $^{31}$P NMR (162 MHz, CDCl$_3$) 40 (m); (d)$^{25}$D −13.7° (c 0.95, CHCl$_3$).

Example 7 (As Depicted in Scheme 4 and Shown as Compound Ia)

Synthesis of Free Phosphine Ligand 1,2-bis((1S,2S)-2-benzylphospholano)-ethane

The 1,2-bis((1S,2S)-2-benzylphospholano borane)-ethane product of Example 6 (100 mg, 0.2439 mmole) was dissolved in 5 mL degassed $CH_2Cl_2$ in a schlenk tube under $N_2$. The solution was cooled to 0° C., and then $HBF_4.Me_2O$ (0.45 mL, 3.66 mmole) was added dropwise via syringe. The reaction was then warmed to room temperature and stirred overnight. The reaction was quenched with a degassed mixture of 6 mL $Et_2O$ and 6 mL saturated $K_2CO_3$. The aqueous layer was removed via pipette while $N_2$ was blown across the solution. The organic layer was washed with 5 mL degassed brine. The aqueous layer was removed via pipette and the organic layer was dried over $MgSO_4$ and then filtered through basic alumina. The solvent was evaporated in vacuo to yield the free phosphine ligand as the sole product. The free phosphine ligand was immediately bound to rhodium as described in the next step to prevent oxidation. $^1$H NMR (400 MHz, $CDCl_3$) δ 0.78–0.99 (m, 4 H), 1.18–1.32 (m, 6 H), 1.53–1.60 (m, 4 H), 1.79–1.82 (m, 6 H), 2.62–2.69 (m, 4 H), 7.11–7.13 (m, 6 H), 7.18–7.22 (m, 4 H); $^{31}$P NMR (162 MHz, $CDCl_3$) −7.9.

Example 8 (As Depicted in Scheme 7 and Shown as Compound IXa)

Synthesis of Rhodium/1,2-bis((1S,2R)-2-benzylphospholano)-ethane Complex

In a 25-mL vial was placed $AgBF_4$ (38 mg, 0.1951 mmole) and chloronorbornadiene rhodium(I) dimer (45 mg, 0.09756 mmole of complex) and 4 mL of distilled THF under $N_2$. The reaction was stirred for 10 minutes. White AgCl fell out of solution. The solution was filtered via syringe filter into another 25-mL vial under $N_2$. The solution was then cooled to −15° C. and the free phosphine ligand of Example 7 was added dropwise via syringe in 4 mL THF. The reaction was then warmed to room temperature and over 1.5 hours the metal complex fell out of solution. The orange chunky catalyst was collected on a frit under vacuum and was washed with Et2O. The catalyst weighed 75 mg/58%. The catalyst was kept under vacuum or in the freezer under $N_2$ until use. $^{31}$P NMR (162 MHz, $CDCl_3$) δ 66.5 (d, $J_{Rh-P}$=144.6 Hz).

X-ray quality crystals were obtained by dissolving 25 mg of the isolated catalyst in a minimal amount of methanol and then blowing a soft stream of $N_2$ across the methanol solution until enough methanol evaporated so that red crystalline cubes formed. X-ray crystallography confirmed the structure and stereochemistry of the catalyst.

Example 9 (As Depicted in Scheme 9 and Shown as Compound 3)

Synthesis of (R)-γ-benzyl-lactone

Sodium metal (6.43 g, 0.28 mole) was dissolved in 200 mL EtOH. To the solution was added 100 mL anhydrous THF. Diethylmalonate (51 mL, 0.33 mole) was poured into the reaction and the reaction was stirred for 5 minutes and then cooled to 0° C. in an ice bath. (S)-(2,3-Epoxypropyl) benzene (15 g, 0.11 mole) was then added quickly via syringe and the ice bath was removed. The reaction was then stirred overnight at room temperature. During the course of the reaction the reaction mixture turned from a clear solution to a white gel. This gel could be stirred magnetically. The reaction was followed by $^1$H-NMR, and after stirring overnight, only the 2 diastereomers of α-ethylcarboxylate-γ-benzyl-lactone and non-reacted diethylmalonate were present. To the reaction was added 60 mL 5N HCl to make the reaction pH=5. The reaction could be backtitrated with 1N NaOH if it became too acidic. The volatiles were then removed under reduced pressure on a rotary evaporator leaving a yellow oil suspended in water. To the suspension was added 65 mL DMSO and then the flask was heated to 150° C. in an oil bath. As water boiled out of the reaction mixture, the reaction temperature increased. After 16 hours the decarboxylation was complete. The reaction was cooled to 0° C. and then 300 mL deionized water was added. The resulting solution was extracted 3 times with 150 mL diethyl ether. The combined diethyl ether layers were then washed with 400 mL deionized water, separated, and then dried over MgSO4. The product lactone, (R)-γ-benzyl-lactone, weighed 20 g (>100% yield) but contained a small amount of diethylmalonate impurity. The product had sufficient purity to be used in the next reaction. Chiral HPLC analysis (Chiralcel OD-H, 80% hexane/20% isopropanol, 1.0 mL/min, 214 nm UV detection, (S) enantiomer eluting at 8.02 minutes and (R) enantiomer eluting at 8.89 minutes) showed 97.1% e.e. (R)-γ-benzyl-lactone. $^1$H NMR (400 MHz, $CDCl_3$) δ 1.90–2.00 (m, 1 H), 2.21–2.29 (m, 1 H), 2.33–2.51 (m, 2 H), 3.07 (dd, J=14.16 Hz, J=6.10 Hz, 1 H), 3.48 (dd, J=14.16 Hz, J=7.08 Hz, 1 H), 4.12–4.77 (m, 1 H), 7.19–7.34 (m, 5 H).

Example 10 (As Depicted in Scheme 9 and Shown as Compound 4)

Synthesis of (R)-1-phenyl-2,5-pentanediol

Lithium aluminum hydride (4.6 g, 0.12 mole) was placed in a 1 liter round bottom flask equipped with a 500 mL pressure equalizing dropping funnel and then 300 mL anhydrous THF was added. The flask was purged with nitrogen. (R)-γ-benzyl-lactone of Example 9 (17.7 g, 0.1 mole) was dissolved in 300 mL anhydrous THF and placed in the dropping funnel. The reaction flask was cooled to 0° C. in an ice bath and then the lactone was added dropwise via the dropping funnel over a period of 30 minutes. After addition the reaction was warmed to room temperature and then stirred overnight. The reaction was cooled to 0° C. and then quenched cautiously with 1N HCl. Deionized water (200 mL) was then added to the reaction mixture and then the mixture was transferred to a separatory funnel. The aqueous solution was extracted 3 times with 200 mL EtOAc. The combined organic layers were then washed successively with 1N HCl, saturated NaHCO3, brine, and then deionized water. The organic layer was dried over $MgSO_4$. The volatiles were removed in vacuo yielding 13.6 g of yellow oil. The diol was then distilled at 178° C./8 mm to yield 10.1 g (61%) (R)-1-phenyl-2,5-pentanediol. Chiral HPLC analysis (Chiralcel OD-H, 80% hexane/20% isopropanol, 1.0 mL/min, 214 nm UV detection, (S) enantiomer eluting at 4.78 minutes and (R) enantiomer eluting at 5.20 minutes) showed 94.5% e.e. (R)-1-phenyl-2,5-pentanediol. $^1$H NMR (400 MHz, $CDCl_3$) δ 1.51–1.58 (m, 1 H), 1.69–1.77 (m, 3 H), 2.12 (br s, 2 H), 2.70 (dd, J=13.4 Hz, J=8.5 Hz, 1 H), 2.82 (dd, J=13.7 Hz, J=4.4 Hz, 1 H), 3.63–3.72 (m, 2 H), 3.83–3.89 (m, 1 H), 7.20–7.33 (m, 5 H); $^{13}$C NMR (100 MHz, $CDCl_3$) δ 29.7, 34.0, 44.2, 63.2, 72.8, 126.8, 129.0, 129.7, 138.5.

Example 11 (As Depicted in Schemes 9, 10 and Shown as Compound 5)

Synthesis of (R)-1-phenyl-2,5-pentanedimesylate

The chiral diol, (R)-1-phenyl-2,5-pentanediol of Example 10 (10.1 g, 0.061 mole), was dissolved in 300 mL $CH_2Cl_2$ in a 1 liter round bottom flask equipped with a pressure equalizing dropping funnel. The flask was purged with nitrogen and then the solution was cooled to 0° C. using an ice bath. To the solution was added Et$_3$N (21.3 mL, 0.15 mole) via syringe. Methanesulfonylchloride (10.4 mL, 0.135 mole) was dissolved in 50 mL CH$_2$Cl$_2$ and placed in the dropping funnel. It was delivered to the diol solution over a period of 30 minutes. After addition, the reaction was stirred 30 minutes at 0° C. and then warmed to room temperature and stirred for 4 hours. The reaction was cooled to 0° C. and then quenched cautiously with 1N HCl. To this quenched solution was added 100 mL 1N HCl and then the reaction mixture was transferred to a separatory funnel. The CH$_2$Cl$_2$ layer was separated. The aqueous layer was extracted with 300 mL CH$_2$Cl$_2$ and then the combined CH$_2$Cl$_2$ layers were washed successively with 1N HCl, saturated NaHCO$_3$, brine, and deionized water. The organic layer was dried over MgSO$_4$ and then the solvent was removed in vacuo yielding 18.5 g (90%) (R)-1-phenyl-2,5-pentanedimesylate. The compound was used in the next step without further purification. $^1$H NMR (400 MHz, CDCl$_3$) δ 1.82–2.03 (m, 6 H), 2.43 (s, 3 H), 3.00 (s, 3 H), 4.27 (m, 2 H), 4.89 (m, 1 H), 7.23–7.32 (m, 3 H), 7.33–7.35 (m, 2 H).

Example 12 (As Depicted in Scheme 10 and Shown as Compound 8)

Synthesis of (1R,2S)-1-methyl-2-benzyl-phospholane borane

Methylphosphine borane was distilled trap-to-trap under high vacuum at room temperature prior to the reaction. The receiving trap was kept at −78° C. during distillation. The methylphosphine borane was weighed quickly in air (4.1 g, 0.065 mole) and then dissolved in 600 mL anhydrous THF in a 2 L round bottom flask. The flask was purged with nitrogen and then the solution was cooled to −78° C. in a dry ice/acetone bath. To the solution was added n-BuLi (52 mL, 0.13 mole) via syringe over a period of 2 to 3 minutes. The reaction was stirred for 1 hour at −78° C. Into a separate 500 mL round bottom flask was dissolved (R)-1-phenyl-2,5-pentanedimesylate of Example 11 (18.2 g, 0.054 mole) in 300 mL anhydrous THF under nitrogen. The dimesylate solution was then added to the methylphosphine borane anion over a period of 2 to 3 minutes via cannula. The reaction was allowed to warm to room temperature over 2 hours and then stirred overnight. The reaction was quenched with 1N HCl and then 600 mL diethyl ether was added to the reaction mixture. The reaction mixture was transferred to a separatory funnel. The organic layer was separated and then it was washed with 1N HCl, brine, and then deionized water. After drying over MgSO$_4$ the volatiles were removed in vacuo to yield 13 g of a yellow oil. Typical reaction mixtures contain 35% of each phospholane diastereomer. Analytical HPLC separations could be accomplished using a 150×4.6 mm BDS-Hypersil-C18 column (5 μm particle size, 120 angstrom pore size) using 65% acetonitrile/35% water as eluent, UV detection at 214 nm, and a 1 mL/min column flow. The title compound, (1R, 2S)-1-methyl-2-benzyl-phospholane borane, eluted at 4.891 minutes and (1S, 2S)-1-methyl-2-benzyl-phospholane borane eluted at 4.559 minutes. The diastereomers could also be separated analytically via chiral HPLC using a Chiracel OD-H column using 80% hexane/35% isopropanol as eluent, UV detection at 214 nm, and a 1 mL/min column flow. The title compound, (1R, 2S)-1-methyl-2-benzyl-phospholane borane, eluted at 4.804 minutes and (1S, 2S)-1-methyl-2-benzyl-phospholane borane eluted at 5.841 minutes. TLC using 1.5% EtOAc/hexane gives indistinguishable separation, but TLC using 5% EtOAc/hexane showed desired diastereomer with Rf=0.18 and undesired diastereomer with Rf=0.15. At higher spotting concentrations, these spots overlap, but lower concentrations show completely resolved spots. Diastereomers were separated via column chromatography over 230 to 400 mesh silica gel on 13 g of this reaction mixture. A 3.5 inch diameter column was used packed with 7.5 inches silica gel/hexane slurry (1.5% EtOAc/hexane eluent, 200 mL fractions).

(1R, 2S)-1-methyl-2-benzyl-phospholane borane (Compound 8):

$^1$H NMR (400 MHz, CDCl$_3$) δ 0.05–0.97 (br m, 3 H), 1.25 (d, J=10.7 Hz), 1.42–1.70 (m, 2 H), 1.70–2.20 (m, 5 H), 2.64–2.73 (m, 1 H), 3.06–3.13 (m, 1 H), 7.17–7.29 (m, 5 H); $^{13}$C NMR (100 MHz, CDCl$_3$) δ 11.8 (d, J$_{C-P}$=31.3 Hz), 24.4, 25.8 (d, J$_{C-P}$=37.4 Hz), 25.8, 33.2, 35.4, 41.0 (d, J$_{C-P}$=33.6 Hz), 41.0, 126.3, 128.5, 128.8, 140.5 (d, J$_{C-P}$=11.5 Hz); $^{31}$P (162 MHz, CDCl$_3$) δ 29.4 (m).

(1S, 2S)-1-methyl-2-benzyl-phospholane borane (Compound 9):

$^1$H NMR (400 MHz, CDCl$_3$) δ 0.19–1.00 (br m, 3 H), 1.30 (d, J=10.3 Hz, 3 H), 1.38–1.44 (m, 1 H), 1.61–1.74 (m, 2 H), 1.96–2.10 (m, 3 H), 2.21–2.26 (m, 1 H), 2.43–2.51 (m, 1 H), 3.03–3.09 (m, 1 H), 7.19–7.33 (m, 5 H); $^{13}$C NMR (100 MHz, CDCl$_3$) δ 7.9 (d, J$_{C-P}$=29.8 Hz), 24.7, 25.9 (d, J$_{C-P}$=35.9 Hz), 32.7, 34.8, 39.8 (d, J$_{C-P}$=34.3 Hz), 126.8, 128.8, 139.9, 140.0; $^{31}$P (162 MHz, CDCl$_3$) δ 27.8 (m).

Example 13 (Shown as Compound 7 in Scheme 10)

Synthesis of 1-phenyl-2,5-pentanediol cyclic sulfate

This procedure was modified from a general procedure for the synthesis of cyclic sulfates as described in the *Journal of the American Chemical Society*, 1991;113:8518–8519. To a solution of 1-phenyl-2,5-pentanediol (5 g, 30.1 mmole) in 180 mL CH$_2$Cl$_2$ was added SOCl2 (2.75 mL, 37.8 mmole) via syringe. The resulting solution was refluxed for 3 hours. After cooling, the volatiles were removed on a rotary evaporator. The residue was dissolved in 45 mL CCl$_4$, 90 mL CH$_3$CN, and 65 mL H$_2$O and the mixture was cooled to 0° C. in an ice bath. To the solution was added RuCl$_3$ (150 mg) followed by NaIO$_4$ (8.1 g, 37.8 mmole). The reaction was stirred overnight and then 300 mL deionized water was added to the solution. The mixture was transferred to a separatory funnel and then extracted 3 times with 100 mL Et$_2$O. After a conventional aqueous work-up, the organic layer was dried over MgSO$_4$ and then the volatiles were removed on a rotary evaporator. The crude product could be recrystallized from hot toluene. $^1$H NMR (400 MHz, CDCl$_3$) δ 1.84–2.12 (m, 4 H), 2.93 (dd, J=14.2 Hz, J=6.6 Hz, 1 H), 3.12 (dd, J=13.9 Hz, J=6.6 Hz, 1 H), 4.31–4.36 (m, 1 H), 4.44 (m, 1 H), 4.80–4.86 (m, 1 H), 7.13–7.33 (m, 5 H); $^{13}$C NMR (100 MHz, CDCl3) δ 27.4, 32.1, 41.8, 72.1, 85.4, 127.4, 128.9, 129.8, 135.7; $^{31}$P (162 MHz, CDCl3) δ 29.4 (m).

Example 14

Synthesis of 1,2-bis((1S,2S)-2-benzylphospholano borane)-ethane

The phosphine borane of Example 12 (2.83 g, 13.74 mmole) was dissolved in 80 mL THF under N$_2$ and cooled to −78° C. To this solution was added s-BuLi (11.6 mL, 1.3 M cyclohexane solution reagent) via syringe and the solution turned red. After stirring for 2 hours at −78° C., CuCl$_2$ powder was added to the reaction in one portion with vigorous stirring. The reaction was allowed to warm to room temperature over 2 hours and then was stirred overnight. The mixture was quenched with 100 mL conc. NH$_4$OH and the organic layer was separated. The aqueous layer was then extracted with 3×50 mL EtOAc. The combined organic layers were washed with 5% NH$_4$OH, 1N HCl, and brine. The organic layer was then dried over MgSO$_4$ and the solvent removed on a rotary evaporator. The crude product was recrystallized 3 times from hot isopropanol to yield 1.15 g/41% of the title compound. Chiral HPLC analysis (Chiralcel OD-H, 80% hexane/20% isopropanol, 0.5 mL/min, 214 nm UV detection, 1,2-bis((1R,2R)-2-benzylphospholano borane)-ethane eluted at 12.81 min and 1,2-bis((1S,2S)-2-benzylphospholano borane)-ethane eluted at 16.84 min, and the meso compound eluted at 14.51 min) showed >99% e.e. of 1,2-bis((1R,2S)-2-benzylphospholano borane)-ethane with >98% purity. $^1$H NMR (400 MHz, CDCl$_3$) δ 0.0–1.0 (m, 6 H), 1.15–1.30 (m, 2 H), 1.40–1.60 (m, 6 H), 1.70–1.80 (m, 4 H), 1.90–2.10 (m, 6 H), 2.68–2.78 (m, 2 H), 2.92–2.99 (m, 2 H), 7.16–7.24 (m, 6 H), 7.27–7.31 (m, 4 H).

Example 15 (Compound Ib)
Synthesis of Free Phosphine Ligand 1,2-bis((1S,2S)-2-benzylphospholano)-ethane The borane protected ligand, 1,2-bis((1S,2S)-2-benzylphospholano borane)-ethane (100 mg, 0.2439 mmole) was dissolved in 5 mL degassed CH$_2$Cl$_2$ in a schlenk tube under N$_2$. The solution was cooled to 0° C., and then HBF$_4$.Me$_2$O (0.45 mL, 3.66 mmole) was added dropwise via syringe. The reaction was then warmed to room temperature and stirred overnight. The reaction was quenched with a degassed mixture of 6 mL Et$_2$O and 6 mL saturated K$_2$CO$_3$. The aqueous layer was removed via pipette while N$_2$ was blown across the solution. The organic layer was washed with 5 mL degassed brine. The aqueous layer was removed via pipette and the organic layer was dried over MgSO4 and then filtered through basic alumina. The solvent was evaporated invacuo to yield the free phosphine as the sole product. The free phosphine was bound to rhodium immediately in the next step to prevent oxidation. 1H NMR (400 MHz, CDCl$_3$) δ 0.78–0.99 (m, 4 H), 1.18–1.32 (m, 6 H), 1.53–1.60 (m, 4 H), 1.79–1.82 (m, 6 H), 2.62–2.69 (m, 4 H), 7.11–7.13 (m, 6 H), 7.18–7.22 (m, 4 H); $^{31}$P NMR (162 MHz, CDCl$_3$) −7.9.

Example 16 (As Depicted in Scheme 11 and Shown as Compound IXc)
Synthesis of Rhodium/1,2-bis((1R,2S)-2-benzylphospholano)-ethane Complex In a 25 mL vial was placed [Rh(norbornadiene)2]+BF4− (0.448 mmole) under nitrogen. To the metal complex was added 2 mL MeOH via syringe and the resulting solution was cooled to −15° C. In a separate vial, the ligand (0.448 mmole) was dissolved in 4 mL THF under nitrogen and then the resulting solution was taken up in a syringe. The ligand solution was added dropwise to the metal complex solution over a period of 5 minutes. The resulting solution was then allowed to warm to room temperature and was stirred for 2 hours. The solvent was removed in vacuo and then the red powder was recrystallized from hot methanol yielding 213 mg/70% of the catalyst IXc. X-ray quality crystals were grown from slow evaporation of a methanol solution of the catalyst. X-ray crystallography confirmed the structure and stereochemistry of the title catalyst. $^{31}$P NMR (162 MHz, CDCl$_3$) δ 66.5 (d, J$_{Rh-P}$=144.6 Hz).
[Rh(norbornadiene)$_2$]$^+$BF$_4^-$ was acquired from Johnson Matthey, Inc. located in Taylor, Mich.

Asymmetric Hydrogenation Reactions

General Procedure and Example: Asymmetric Hydrogenation of Substrates

A variety of substrates were catalyzed with Compound IXc. The substrates include methyl 2-acetamidoacrylate, 2-acetamidoacrylic acid, α-acetamidocinnamic acid, and 3-cyano-5-methylhex-3-enoic acid. These compounds are generically referred to as "substrate" and the reaction schemes are shown in Schemes 14 to 17.

Compound IXc (0.01 mmole) was dissolved in 1 mL of methanol in a Griffin-Worden pressure vessel equipped with the attachments necessary to connect to a lecture bottle. The substrate (1 mmole) was dissolved in 3 mL of the same solvent and this was delivered to the catalyst solution. The solution was freeze-pump-thaw-degassed for one cycle and then the reaction solution was warmed to 25° C. The vessel was then pressurized to 30 psi hydrogen. Reaction completion times and enantiomeric excesses were monitored by chiral GC. After reaction completion, which ranged from about 15 to 45 minutes, only hydrogenation products were observed.

Enantiomeric Excess Determinations

Enantiomeric excess determinations were carried out via chiral gas chromatography.
N-Acetylalanine Methyl Ester Enantiomers are separated using a chiral 40 m B-TA Chiraldex column. Conditions are 120° C. isothermal for 20 minutes, injector temperature 200° C., detector temperature 225° C., split ratio >100:1, helium carrier gas 65 mL/min. Enantiomers are separated at 12.811 minutes and 14.196 minutes.
N-Acetylalanine The methyl ester of this compound is made by treating N-acetylalanine in methanolic solution with excess trimethylsilyldiazomethane. The enantiomeric excess of the resulting methyl ester is analyzed as delineated for N-acetylalanine methyl ester.
N-Acetylphenylalanine The methyl ester of this compound is made by treating N-acetylphenylalanine in methanolic solution with excess trimethylsilyldiazomethane. The resulting methyl ester is analyzed via chiral HPLC using a Chiracel OJ column.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds.

The present invention should not be considered limited to the particular examples described above, but rather should be understood to cover all aspects of the invention as fairly set out in the attached claims. Various modifications, equivalent processes, as well as numerous structures to which the present invention may be applicable will be readily apparent to those of skill in the art to which the present invention is directed upon review of the instant specification.

What is claimed is:
1. A chiral catalyst of the formula

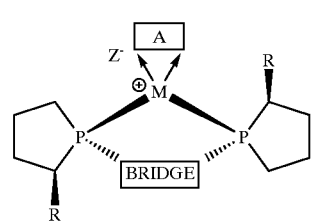

IX and its corresponding enantiomer, wherein:
R is an aikyl, fluoroalkyl, or perfluoroalkyl group each containing up to about 8 carbon atoms, a carboxylic acid group, a carboxylic ester group, an aryl group, a substituted atyl group, an aralkyl group, or a ring substiuxted aralkyl group;

a Bridge is a —(CH$_2$)$_n$— where n is an integer from 1 to 12, a 1,2-divalent phenyl, or a 1,2-divalent substituted phenyl;

M is a transition metal;

Z is BF$_4$, PF$_6$, SbF$_6$, OTf, or ClO$_4$; and

A is norbornadjene or cyclooctadiene.

2. The chiral catalyst of claim 1, wherein M is rhodium.

3. The chiral catalyst of claim 1, wherein Z is BF$_4$.

4. The chiral catalyst of claim 1, wherein A is norborraadiene.

5. A method for an asymmetric transformation comprising the step of reacting a substrate with a compound of the formula

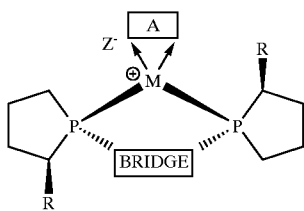

IX or its corresponding enantiomer, or a solvate thereof, wherein:

R is an alkyl, fluoroalkyl, or perfluoroallcyl group each containing up to about 8 carbon atoms, a carboxylic acid group, a carboxylic ester group, an azyl group, a substituted azyl group, an aralkyl group, or a ring substituted aralkyl group;

a Bridge is a —(CH$_2$)$_n$— where n is an integer from 1 to 12, a 1,2-divalent phonyl, or a 1,2-divalent substituted phenyl;

M is a transition metal;

Z is BF$_4$, PF$_6$, SbF$_6$, OTf, or ClO$_4$; and

A is norbornadiene or cyclooetadiene;

wherein the asymmetric transformation is selected from the group consisting of hydrogenation, hydroformylation, π-allyl palladium coupling, hydrosilazion, hydrocyanation, olefin metathesis, hydroacylation, and isomerization of allylamines.

6. The method of claim 5, wherein M is rhodium.

7. The chiral catalyst of claim 5, wherein Z is BF$_4$.

8. The chiral catalyst of claim 5, wherein A is norborriadiene.

9. The method of claim 5, wherein the asymmetric transformation is a hydrogenation reaction.

10. The method of claim 5, wherein the substrate is is 3-cyano-5-methylhex-3-enoic acid, or a methyl ester, an ethyl ester, a potassium salt, a lithium salt, a sodium salt, or a t-butylammonium salt thereof.

11. The method of claim 5, wherein a product of the asymmetric transformation has a high degree of enantiomeric excess.

* * * * *